(12) United States Patent
Lyu et al.

(10) Patent No.: US 7,858,209 B2
(45) Date of Patent: Dec. 28, 2010

(54) FLUORENE-BASED COMPOUND AND ORGANO-ELECTROLUMINESCENT DEVICE USING THE SAME

(75) Inventors: Yi-yeol Lyu, Yongin-si (KR); Che-un Yang, Yongin-si (KR); Young-hun Byun, Yongin-si (KR); O-hyun Kwon, Seoul (KR)

(73) Assignee: Samsung Electronics Co., Ltd. (KR)

( * ) Notice: Subject to any disclaimer, the term of this patent is extended or adjusted under 35 U.S.C. 154(b) by 785 days.

(21) Appl. No.: 11/764,529

(22) Filed: Jun. 18, 2007

(65) Prior Publication Data

US 2008/0048559 A1 Feb. 28, 2008

(30) Foreign Application Priority Data

Aug. 24, 2006 (KR) .................. 10-2006-0080720

(51) Int. Cl.
H01J 1/63 (2006.01)
(52) U.S. Cl. .................. 428/690; 313/504; 428/447
(58) Field of Classification Search .................. None
See application file for complete search history.

(56) References Cited

U.S. PATENT DOCUMENTS

| | | | |
|---|---|---|---|
| 4,356,429 A | 10/1982 | Tang | |
| 4,885,211 A | 12/1989 | Tang et al. | |
| 5,151,629 A | 9/1992 | VanSlyke | |
| 7,064,228 B1 * | 6/2006 | Yu et al. | 556/489 |
| 2005/0164034 A1 * | 7/2005 | Park et al. | 428/690 |
| 2006/0177691 A1 | 8/2006 | Tai et al. | |

FOREIGN PATENT DOCUMENTS

KR  1999003782  1/1999

OTHER PUBLICATIONS

Li, Z.H., et al.; "Synthesis and Functional Properties of End-Dendronized Oligo(9,9-diphenyl)fluorenes"; Organic Letters; vol. 8, No. 7; pp. 1499-1502; 2006.

European Search Report dated Jan. 10, 2008 for Application No. 07113588.3 {all references cited in the Search Report are listed above).

Kuwabara, et al.; "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials"; Advanced Materials; vol. 6, No. 9; pp. 677-679; 1994.

(Continued)

Primary Examiner—D. Lawrence Tarazano
Assistant Examiner—Gregory Clark
(74) Attorney, Agent, or Firm—Cantor Colburn LLP

(57) ABSTRACT

Provided herein are fluorene-based compounds including a fluorene or a spirofluorene structure at both terminals and a spacer including one or more atoms between the both terminals. The invention further provides an organo-electroluminescent device having an organic layer in which the fluorene-based compound is introduced. The fluorene-based compound can be readily manufactured using dry and wet processes, and the organo-electroluminescent device using the same has excellent properties in color purity, internal and external efficiency, and thermal, optical and electric stability.

32 Claims, 3 Drawing Sheets

OTHER PUBLICATIONS

Pei, et al.; "Head-to-Tail Regioregular Oligothiophene-Functionalized 9,9'-Spirobufluorene Derivatives. 1. Synthesis"; J. Org. Chem.; vol. 67; pp. 4924-4936; 2002.

Wong, et al.; "Synthesis and Properties of Novel Thiophene-Based Conjugated Homologues: 9,9-Diphenylfluorene-Capped Olgithiophenes"; Organic Letters; vol. 4, No. 25; pp. 4439-4442; 2002.

Wong, et al.; "Spiro-Configured Biflourenes: Highly Efficient Emitter for UV Organic Light-Emitting Device and Host Material for Red Electrophosphorescence"; Organic Letters; vol. 7, No. 23; pp. 5131-5134; 2005.

* cited by examiner

FLUORENE-BASED COMPOUND AND ORGANO-ELECTROLUMINESCENT DEVICE USING THE SAME

This application claims priority to Korean Patent Application No. 10-2006-0080720, filed on Aug. 24, 2006, and all the benefits accruing therefrom under 35 U.S.C. §119, the content of which is incorporated herein by reference in its entirety.

BACKGROUND OF THE INVENTION

1. Field of the Invention

The present invention relates to a fluorene-based compound and an organo-electroluminescent device using the same. In particular, the invention relates to a fluorene-based compound comprising a fluorene or a spirofluorene structure at both terminals, and a spacer including one or more atoms between the terminal fluorene or spirofluorene structures. The invention is further directed to an organo-electroluminescent device having an increased internal and external light emitting efficiency and improved color purity by forming high quality organic layers through dry and wet processes using the fluorene-based compound.

2. Description of the Related Art

Organo-electroluminescent devices are active light emitting display devices that emit light by recombination of electrons and holes in a thin layer made of a fluorescent or phosphorescent compound (an organic layer) when a current is applied to the organic layer. The organo-electroluminescent devices have various advantages, such as being lightweight, having simple constitutional elements, and having a simple fabrication process, while providing a superior image quality and wide viewing angle. Furthermore, the organo-electroluminescent devices can create nearly perfect dynamic images having high color purity. The organo-electroluminescent devices also have electrical properties making them suitable for use in portable electronic equipment, such as low power consumption and low driving voltage.

Organo-electroluminescent devices are known in the art. For example, a multi-layered organo-electroluminescent device using an aluminum quinolinol complex layer and a triphenylamine derivative layer was developed by Eastman Kodak Co. (U.S. Pat. No. 4,885,211). In another example, a wide range of light from ultraviolet light to infrared light can be emitted using low-molecular weight organo-electroluminescent materials (U.S. Pat. No. 5,151,629).

Light emitting devices, which are self-illuminated light emitting display devices in contrast to backlit displays with an independent light source, have wide viewing angles, excellent contrast and quick response. Such light emitting devices can be classified into inorganic light emitting devices using inorganic compounds to form emitting layers and organic light emitting devices ("OLED") using organic compounds to form emitting layers. Organic light emitting devices are brighter, have lower driving voltages and quicker responses than inorganic light emitting devices. Furthermore, organic light emitting devices can realize multiple colors. For these reasons, organic light emitting devices are being actively studied.

Conventionally, an OLED has a layered or laminated structure. For example, a typical OLED has an anode/organic emitting layer/cathode multilayered structure. An OLED can also have various other structures, such as an anode/hole injection layer/hole transport layer/emitting layer/electron transport layer/electron injection layer/cathode multilayered structure or an anode/hole injection layer/hole transport layer/emitting layer/hole blocking layer/electron transport layer/electron injection layer/cathode multilayered structure.

Materials that are used in organic light emitting devices can be classified into vacuum deposited materials and solution coated materials according to a method of preparing an organic layer. The vacuum deposited materials may have a vapor pressure of greater than or equal to about $10^{-6}$ torr, at a temperature of 500° C. or less and are low molecular materials having a molecular weight of 1,200 g/mol or less. The solution coated materials may be highly soluble in solvents which are prepared in a solution phase. Solution coated materials can include aromatic or heterocyclic groups.

When the vacuum deposition is used to prepare an organo-electroluminescent device, the manufacturing costs are increased due to the cost of using a vacuum system. In addition, when a shadow mask is used to prepare pixels to display natural colors, pixels having high resolution are not readily produced.

On the other hand, solution coatings can be formed readily by spin coating or by printing, such as by inkjet printing and screen printing. Accordingly, organo-electroluminescent devices can be fabricated using solution coatings in a simplified manner and at a lower cost. Using the solution coatings, relatively high quality resolution can be obtained compared to the shadow mask.

However, materials that are used in solution coatings can have lower thermal stability which can result in e.g., lower color purity, and other compromised properties than would those deposited by vacuum deposition methods. In addition, the materials used in solution coatings can be crystallized and to provide the resulting particle size from wavelength of visible lights. In this way, a white residue may occur by scattering of the visible light or from the formation of pin holes in the coating, thereby degrading properties of the organic light emitting devices, even though the materials have excellent properties in thermal stability and color purity.

Japanese Patent Publication No. 1999-003782 discloses an anthracene substituted with two naphtyl groups, which can be used as a light emitting layer or a hole injection layer. However, the substituted anthracene is not sufficiently soluble in solvents, and properties of an OLED using the same are unsatisfactory.

Conventional OLED devices thus continue to have several problems including high drive voltage, low color purity and low emission efficiency. Therefore, there remains a need to develop an OLED having properties such as low driving voltage, excellent brightness, light emitting efficiency and color purity using a light emitting compound which has excellent thermal stability and is capable of forming an excellent organic layer formed using a solution coating method.

BRIEF SUMMARY OF THE INVENTION

In one embodiment, the invention provides a fluorene-based compound having excellent thermal stability and light emitting capability in which charges are easily transported and which can be manufactured by either dry or wet processes In another embodiment, the present invention provides an organo-electroluminescent device having improved properties in efficiency, driving voltage and color purity by employing an organic layer having the fluorene-based compound relative to organo-electroluminescent devices that do not include an organic layer having the fluorene-based compound.

According to one embodiment, there is provided a fluorene-based compound represented by Formula 1 or 2 below

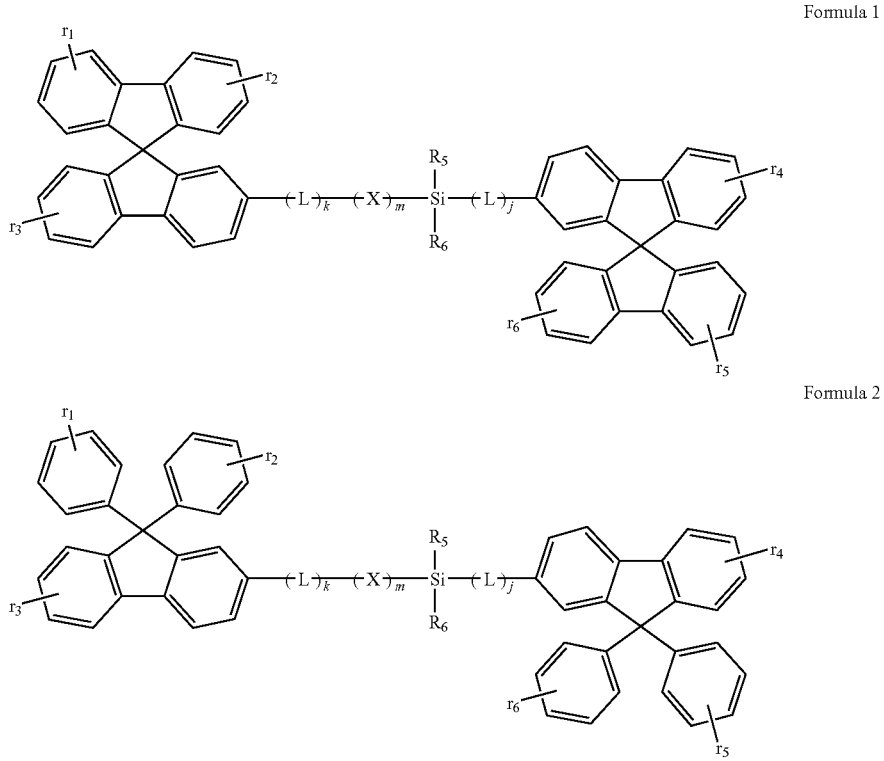

Formula 1

Formula 2

Here, L is a substituted or unsubstituted $C_2$~$C_{30}$ alkylene group, a substituted or unsubstituted $C_6$~$C_{30}$ cycloalkylene group, a substituted or unsubstituted $C_6$~$C_{30}$ arylene group, a substituted or unsubstituted $C_2$~$C_{30}$ heteroarylene group, or a substituted or unsubstituted $C_2$~$C_{30}$ alkenylene group;

k is an integer from 0 to 2, j is an integer from 0 to 2,

X is

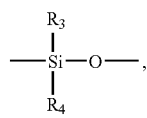

where $R_3$ and $R_4$ are each independently a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, or a substituted or unsubstituted $C_2$~$C_{30}$ heteroaryl group;

m is an integer from 0 to 3, $R_5$ and $R_6$ are each independently a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, or a substituted or unsubstituted $C_2$~$C_{30}$ heteroaryl group;

$r_1$, $r_2$, $r_3$, $r_4$, $r_5$ and $r_6$ are each independently a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, or a substituted or unsubstituted $C_2$~$C_{30}$ heteroaryl group.

According to another embodiment, is the invention provides an organo-electroluminescent device comprising a first electrode; a second electrode; and at least one organic layer disposed between and in at least partial contact with both the first electrode and the second electrode, wherein the organic layer comprises the fluorene-based compound of Formula 1 or 2.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
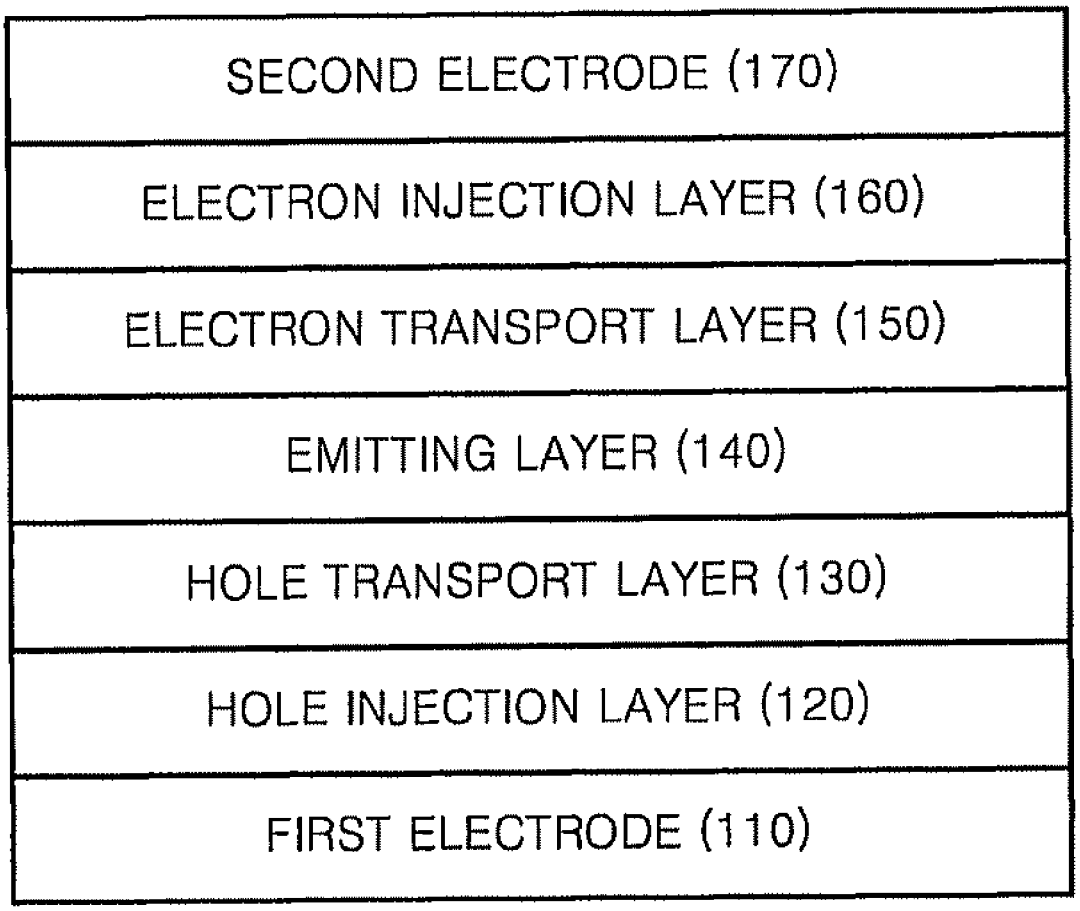
FIGS. 1A through 1C are views schematically illustrating layered structures of the organo-electroluminescent device according to an embodiment of the present invention.

Hereinafter, the present invention will now be described more fully with reference to the accompanying drawings, in which exemplary embodiments of the invention are shown. The invention may, however, be embodied in many different forms and should not be construed as being limited to the embodiments set forth herein. Rather, these embodiments are provided so that this disclosure will be thorough and complete, and will fully convey the concept of the invention to those skilled in the art.

It will be understood that when an element is referred to as being "on" another element, it can be directly on the other element or intervening elements may be present therebetween. In contrast, when an element is referred to as being "disposed on" or "formed on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In one embodiment, the invention provides fluorene-based compounds represented by Formula 1 or 2. The fluorene-based compounds represented by Formula 1 or 2 include a fluorene or spirofluorene structure at both terminal positions; and a spacer including a silicon atom between the both terminals, the presence of which allows for wet coating of the fluorine-based compound and provides thermal stability.

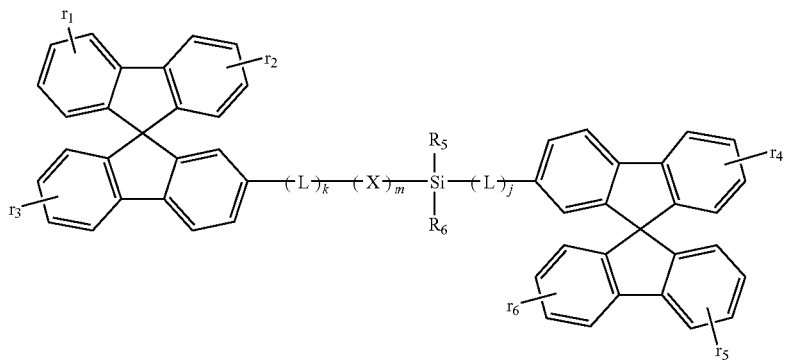

Formula 1

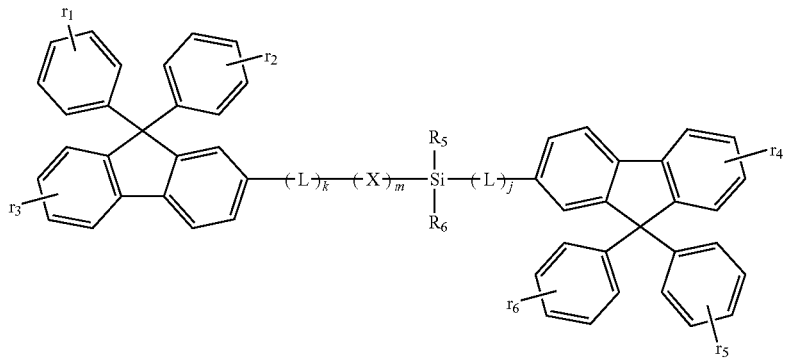

Formula 2

For both structures represented by Formula 1 or 2, L is a substituted or unsubstituted $C_2$~$C_{30}$ alkylene group, a substituted or unsubstituted $C_6$~$C_{30}$ cycloalkylene group, a substituted or unsubstituted $C_6$~$C_{30}$ arylene group, a substituted or unsubstituted $C_2$~$C_{30}$ heteroarylene group, or a substituted or unsubstituted $C_2$~$C_{30}$ alkenylene group;

k is an integer from 0 to 2, j is an integer from 0 to 2,

X is

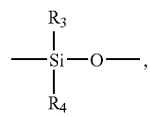

where $R_3$ and $R_4$ are each independently a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, or a substituted or unsubstituted $C_2$~$C_{30}$ heteroaryl group;

m is an integer from 0 to 3, $R_5$ and $R_6$ are each independently a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, or a substituted or unsubstituted $C_2$~$C_{30}$ heteroaryl group;

$r_1$, $r_2$, $r_3$, $r_4$, $r_5$ and $r_6$ are each independently a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, or a substituted or unsubstituted $C_2$~$C_{30}$ heteroaryl group.

Where an aryl group is indicated for $R_5$, $R_6$, and $r_{1-6}$ "aryl" means a monovalent hydrocarbon group having an aromatic ring system. An aryl group may have two or more ring systems which can bind to each other or be fused together. Similarly, where a heteroaryl group is indicated for $R_5$, $R_6$, and $r_{1-6}$, a "heteroaryl" group indicates an aryl group in which at least one of carbons is substituted with an atom selected from the group consisting of N, O, S, and P.

Also, where a cycloalkyl group is indicated for $R_5$, $R_6$, and $r_{1-6}$, the cycloalkyl group is an alkyl group having a ring system, and similarly a heterocycloalkyl group indicates an cycloalkyl group in which at least one of carbons are substituted with an atom selected from the group consisting of N, O, S, and P.

In Formula 1 and 2, the alkyl group, the alkoxy group, the aryl group, the heteroaryl group, the cycloalkyl group and the heterocycloalkyl group can be substituted. The substituent may include at least one selected from the group consisting of —F, —Cl, —Br, —CN, —$NO_2$, and —OH; a $C_1$~$C_{20}$ alkyl group unsubstituted or substituted by —F, —Cl, —Br, —CN, —$NO_2$ or —OH, a $C_1$~$C_{20}$ alkoxy group unsubstituted or substituted by —F, —Cl, —Br, —CN, —$NO_2$ or —OH, a $C_6$~$C_{30}$ aryl group unsubstituted or substituted by —F, —Cl, —Br, —CN, —$NO_2$ or —OH, a $C_2$~$C_{30}$ heteroaryl group unsubstituted or substituted by —F, —Cl, —Br, —CN, —$NO_2$ or —OH, a $C_5$~$C_{20}$ cycloalkyl group unsubstituted or substituted by —F, —Cl, —Br, —CN, —$NO_2$ or —OH, and a $C_5$~$C_{30}$ heterocycloalkyl group unsubstituted or substituted by —F, —Cl, —Br, —CN, —$NO_2$ or —OH.

According to an embodiment of the present invention, the fluorene-based compound of Formula 1 or 2 includes a spacer having silicon atom between the fluorene or spirofluorene structure at both terminals, providing for increased solubility and amorphous property, and thus film forming capability is improved.

The fluorene-based compound of Formula 1 or 2 may be one compound selected from the group consisting of compounds represented by Formulae 3 to 13.

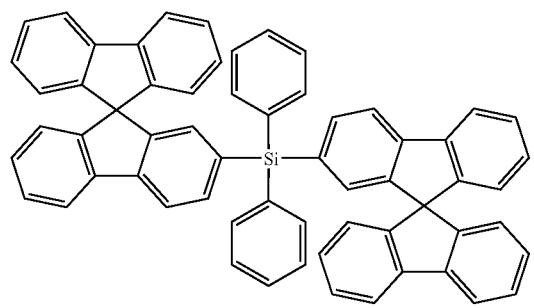

Formula 3

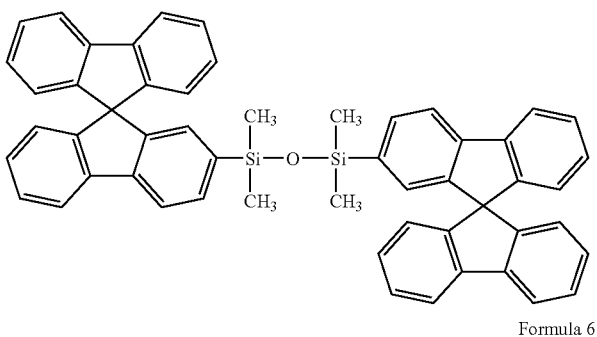

Formula 4

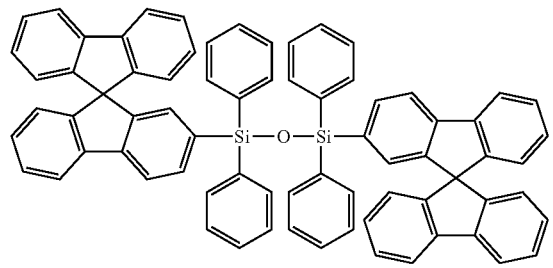

Formula 5

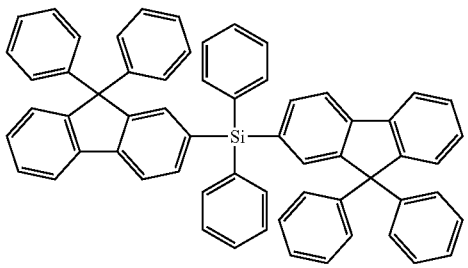

Formula 6

-continued
Formula 7
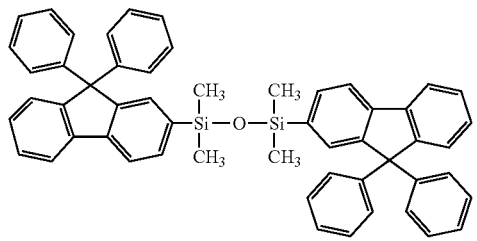
Formula 8
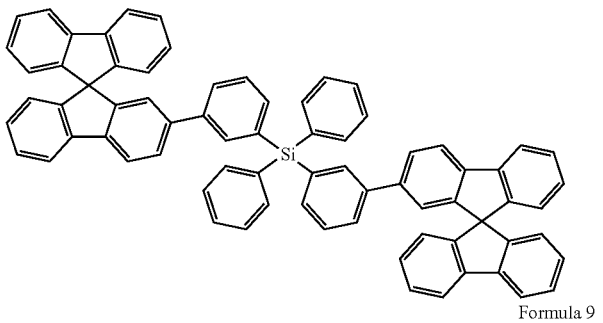
Formula 9
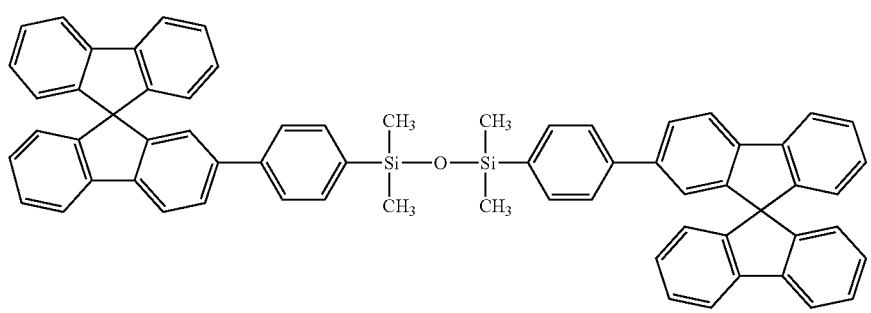
Formula 10
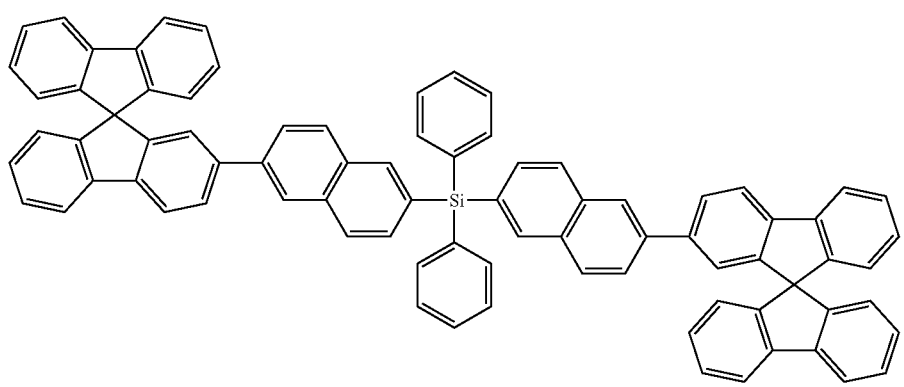
Formula 11
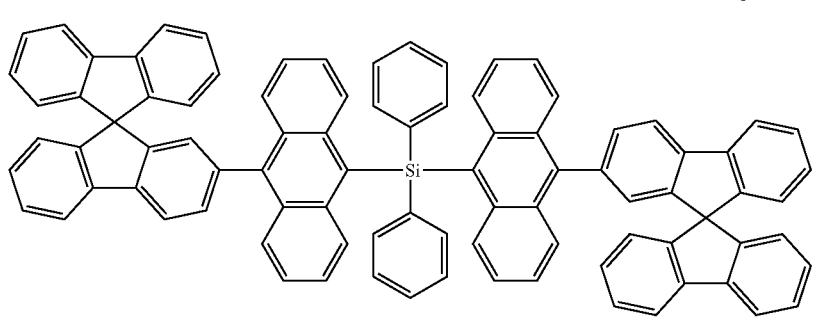
Formula 12
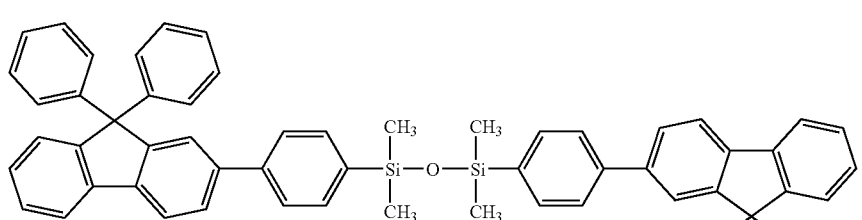

The compound represented by Formula 1 and 2 can be synthesized using any method that is commonly used in the art. Examples of the synthesis of the compound represented by Formula 1 and 2 are described in detail in Reaction Schemes in Synthesis Examples.

In one embodiment, the invention is directed to an organo-electroluminescent device. The organo-electroluminescent device comprises: a first electrode; a second electrode; and an organic layer interposed between the first electrode and the second electrode, wherein the organic layer comprises at least one of compounds represented by Formula 1 and 2.

In one embodiment, the compound of Formula 1 or 2 is suitable for an organic layer of an organo-electroluminescent device, and more particularly for an emitting layer, hole injection layer, or a hole transport layer.

As noted above, the compound of Formula 1 or 2 has excellent solubility, thermal stability, and capability of forming a stable organic layer using a solution coating method. An organo-electroluminescent device comprising an organic layer comprising at least one of compounds represented by Formula 1 and 2, according to an embodiment of the present invention, will have improved light emitting properties in driving voltage, color purity, and the like, when compared with a conventional organo-electroluminescent device in which stability of the organic layer is degraded when the organic layer is prepared using a solution coating.

The structure of the organo-electroluminescent device of an embodiment of the present invention may vary. For example, it is envisioned that organo-electroluminescent device can comprise at least one layer selected from the group consisting of a hole injection layer, a hole transport layer, a hole blocking layer, an electron blocking layer, an electron transport layer, and an electron injection layer between the first electrode and the second electrode.

Figure 1B:
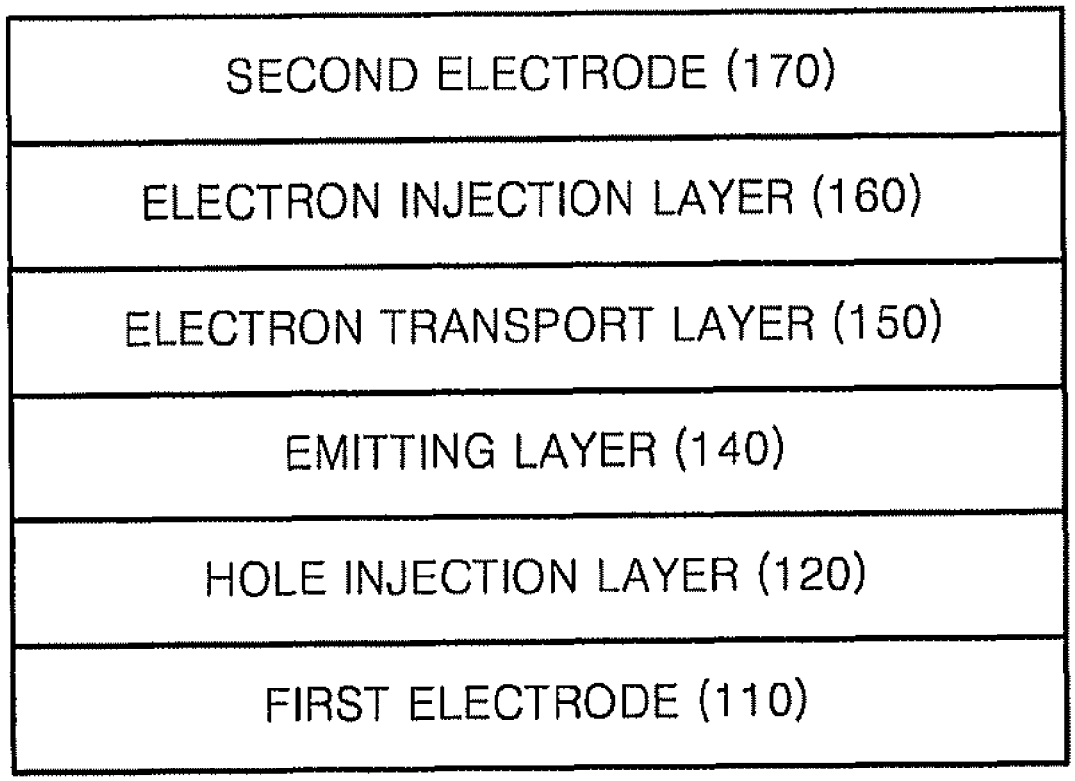
Figure 1C:
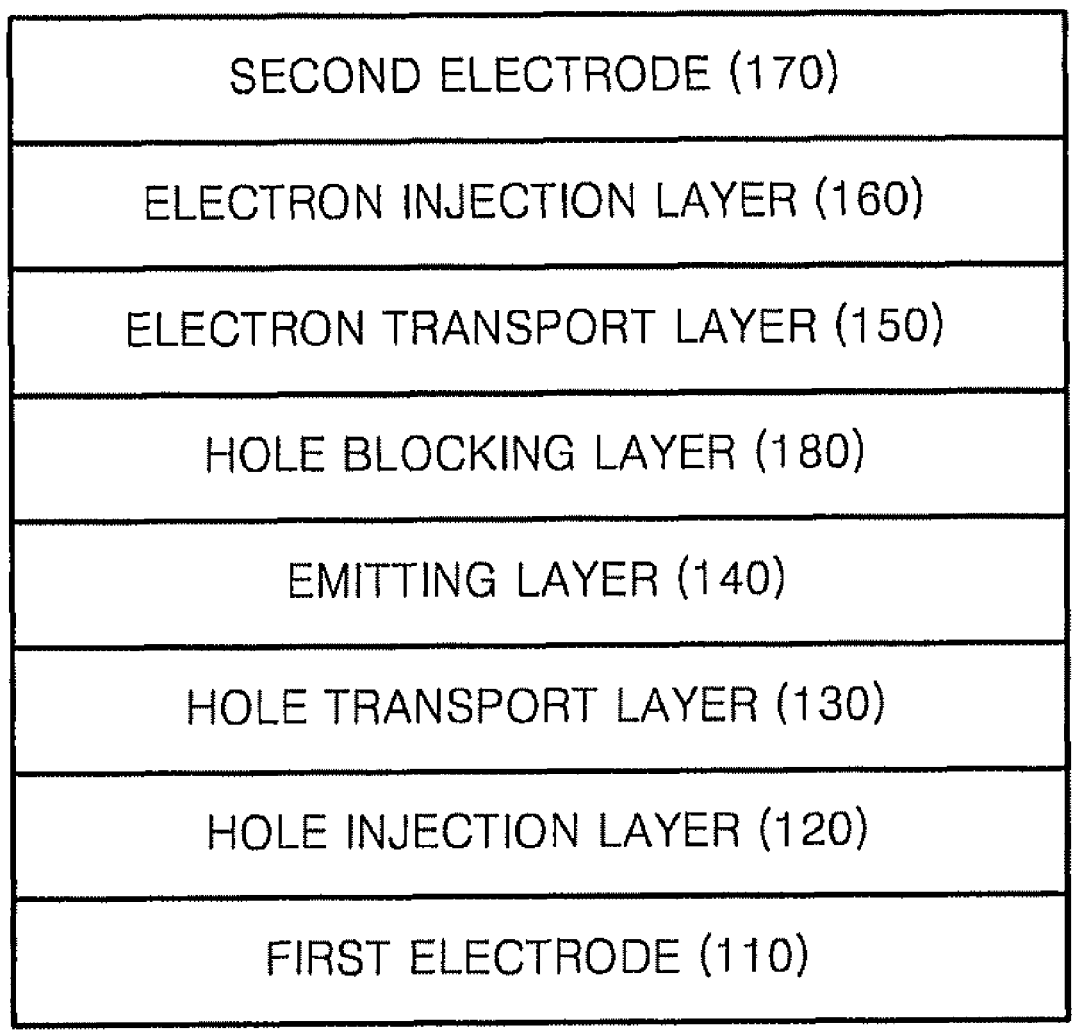

Examples of the organo-electroluminescent device according to alternative embodiments of the present invention are shown in FIGS. 1A, 1B, and 1C. FIGS. 1A through 1C are views schematically illustrating the layered structures of the organo-electroluminescent device according to an embodiment of the present invention. Referring to FIG. 1A, an exemplary organo-electroluminescent device has a layered structure comprising a first electrode 110/hole injection layer 120/hole transport layer 130/emitting layer 140/electron transport layer 150/electron injection layer 160/second electrode 170 structure. Referring to FIG. 1B, an exemplary organo-electroluminescent device has a layered structure comprising a first electrode 110/hole injection layer 120/emitting layer 140/electron transport layer 150/electron injection layer 160/second electrode 170 structure. Referring to FIG. 1C, an exemplary organo-electroluminescent device has a layered structure comprising a first electrode 110/hole injection layer 120/hole transport layer 130/emitting layer 140/hole blocking layer 180/electron transport layer 150/electron injection layer 160/second electrode 170 structure. Here, at least one of the emitting layer 140, hole injection layer 120, and hole transport layer 130 can include a compound of Formula 1 or 2.

In one embodiment, the emitting layer 140 of the organo-electroluminescent device can include a phosphorescent or a fluorescent dopant having red, green, blue or white color. The phosphorescent dopant can be an organic metal compound which contains at least of Ir, Pt, Os, Ti, Zr, Hf, Eu, Tb, or Tm.

According to one embodiment, the organo-electroluminescent device can be manufactured by, but is not limited to, conventional methods. Hereinafter, a method of manufacturing an organo-electroluminescent device, according to an embodiment of the present invention, will be described with reference to the organo-electroluminescent device illustrated in FIG. 1C.

First, a first electrode 110 is formed by depositing, or sputtering, a high work-function material that is used to form the first electrode, on a surface of a substrate (substrate not shown). The first electrode 110 can be an anode.

The substrate, which can be any substrate that is used in conventional organo-electroluminescent devices, can be a glass substrate or a transparent plastic substrate with excellent mechanical strength, thermal stability, transparency, surface smoothness, ease of treatment, and that is waterproof.

In one embodiment, the material used to form the first electrode 110 can be indium tin oxide ("ITO"), indium zinc oxide ("IZO"), stannic oxide ($SnO_2$), zinc oxide (ZnO), or any transparent material, which has high conductivity.

Then, a hole injection layer ("HIL") 120 can be formed on a surface of the first electrode 110 opposite the substrate by vacuum deposition, spin coating, casting, by langmuir blodgeft ("LB") film, or the like. Without being held to theory, it is believed that the hole injection layer 120 increases contact resistance between the first electrode 110 and the emitting layer 140, and improve the hole transporting capacity of the first electrode 110 with respect to the emitting layer 140.

When the HIL 120 is formed by vacuum deposition, vacuum deposition conditions may vary according to the compound that is used to form the HIL 120, and the structure and thermal properties of the HIL 120 to be formed. In general, however, conditions for vacuum deposition can include a deposition temperature of 100-500° C., a pressure of $10^{-8}$-$10^{-3}$ torr, a deposition rate of 0.01-100 Å/sec, and a layer thickness of about 10 Å to about 5 μm.

When the HIL 120 is formed by spin coating, coating conditions may vary according to the compound that is used to form the HIL 120, and the structure and thermal properties of the HIL 120 to be formed. In general, however, the coating spin speed may be from about 2,000 to about 5,000 rpm, and the temperature for heat treatment, which is performed post-spin to remove residual casting solvent after coating, can be from about 80 to 200° C.

In one embodiment, the material used to form the HIL 120 can be a compound of Formula 1 or 2 described above. In another embodiment, any material useful for forming the HIL 120 can also be used. For example, the material used to form the HIL 120 can be a phthalocyanine compound, such as a copper phthalocyanine disclosed in U.S. Pat. No. 4,356,429; a star-burst type amine derivative, such as 4,4',4"-tris(N-carbazolyl)-triphenylamine ("TCTA"), 4,4',4"-tris(3-methylphenylphenylamino)triphenylamine ("m-MTDATA"), and 1,3,4-tris{4-[methylphenyl(phenyl)amino]phenyl}benzene ("m-MTDAPB") disclosed in *Advanced Material* 1994, vol. 6, p. 677; polyaniline/Dodecylbenzenesulfonic acid (Pani/DBSA); poly(3,4-ethylenedioxythiophene)/Poly(4-styrenesulfonate (PEDOT/PSS); polyaniline/camphor sulfonic acid (Pani/CSA); (polyaniline)/poly(4-styrenesulfonate) (PANI/PSS); or the like, and which is a soluble and conductive polymer.

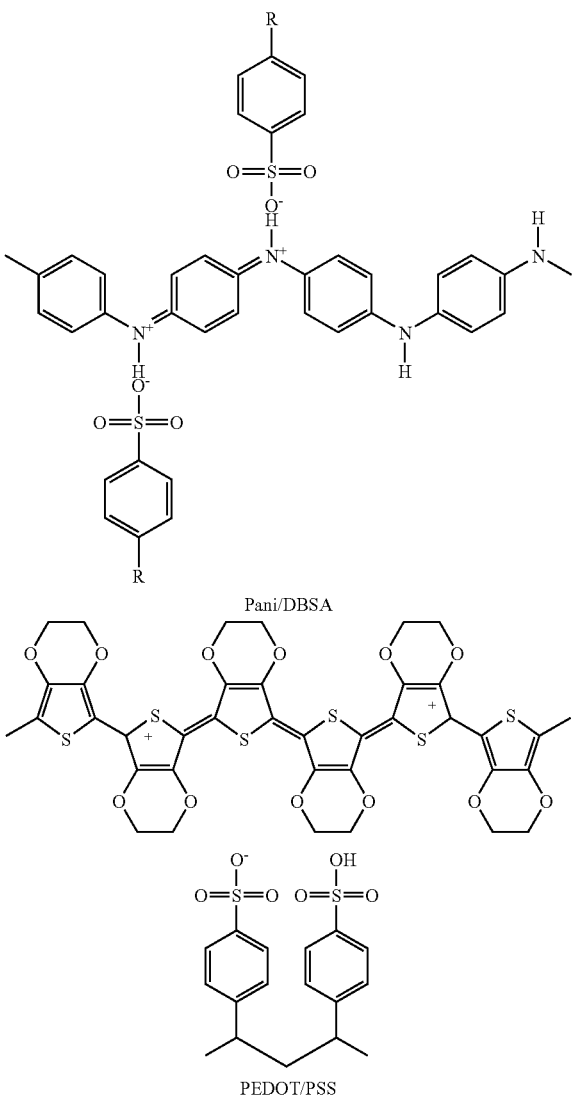

Pani/DBSA

PEDOT/PSS

The thickness of the HIL 120 can be about 100 to about 10,000 Å, and preferably, about 100 to about 1,000 Å. When the thickness of the HIL 120 is less than about 100 Å, the hole injecting capability of the layer may be reduced. On the other hand, when the thickness of the HIL is greater than about 10,000 Å, the driving voltage of the device can increase.

Then, a hole transport layer ("HTL") 130 can be formed on a surface of the HIL 120 opposite the first electrode 110 using a vacuum deposition method, a spin coating method, a casting method, LB, or the like. When vacuum deposition and spin coating are used to form the HTL 130, conditions for deposition and coating are similar to those used for formation of the HIL 120, although conditions for deposition and coating may vary according to the material that is used to form the HTL 130.

In one embodiment, the material used to form the HTL 130 can be a compound represented by Formula 1 described above. In an alternative embodiment, any material that is conventionally used to form an HTL 130 can be used to form the HTL 130. For example, the material used to form the HTL 130 can be a carbazole derivative such as N-phenylcarbazole and polyvinylcarbazole; an amine derivative having an aromatic condensation ring such as N,N'-bis(3-methylphenyl)-N,N'-diphenyl-[1,1-biphenyl]-4,4'-diamine ("TPD") and N,N'-di(naphthalene-1-yl)-N,N'-diphenyl benzidine ("α-NPD"); or the like.

The thickness of the HTL 130 may be from about 50 to about 1,000 Å, and preferably, about 100 to about 600 Å. When the thickness of the HTL 130 is less than about 50 Å, hole transporting capability may be reduced. On the other hand, when the thickness of the HTL 130 is greater than about 1000 Å, the driving voltage of the device can increase.

Then, an emitting layer ("EML") 140 can be formed on a surface of the HTL 130 by vacuum deposition, spin coating, casting, LB, or the like. When the EML is formed by vacuum deposition or spin coating, conditions for deposition and coating are similar to those used for formation of the HIL 120, although conditions for deposition and coating may vary according to the material used to form the EML. In one embodiment, the EML 140 can be formed using the compound represented by Formula 1 or 2 as the host material.

In another embodiment, the host material used to form the EML 140 can be the compound represented by Formula 1 or 2 mixed with a proper fluorescent host material or dopant. Thus, the compound of Formula 1 or 2 can be used as the only phosphorescent host, or the compound of Formula 1 or 2 can be used together with other fluorescent host materials, such as 4,4'-N,N'-dicarbazole-biphenyl ("CBP"), poly(n-vinylcarbazole ("PVK"), or the like.

In another embodiment, the EML 140 can be formed by mixing the EML 140 host material with a dopant. Exemplary phosphorescent dopant materials include, for example, a red phosphorescent dopant such as platinum octaethyl porphine ("PtOEP"), RD 61 obtained from UDC Co., a green phosphorescent dopant such as Ir(PPy)$_3$ (where PPy is 2-phenylpyridine), a blue phosphorescent dopant such as iridium (III) bis[4,6-di-fluorophenyl)-pyridinato-N,C$^{2'}$]picolinate (referred to herein as both "F$_2$Irpic" and "Firpic"), a red phosphorescent dopant such as RD 61 obtained from UDC Co., and the like.

The amount of dopant used in the EML 140 varies according to the host material used to form the EML 140. When the compound of Formula 1 or 2 is used as a dopant, the concentration of the dopant is not limited, but conventionally is from 0.01 to 15 parts by weight based on 100 parts by weight of a host. When the compound of Formula 1 or 2 is used as a sole host, the concentration of the dopant is not limited, but is conventionally from about 0.01 to about 15 parts by weight based on 100 parts by weight of a host. When the compound of Formula 1 or 2 is not used as a sole host, the concentration of the host is from about 30 to about 99 parts by weight based on 100 parts by weight of the total host.

The thickness of the EML 140 can be from about 100 to about 1,000 Å, and preferably, from about 200 to about 600 Å. When the thickness of the EML is less than about 100 Å, light-emitting capability may be reduced. On the other hand, when the thickness of the EML 140 is greater than about 1000 Å, the driving voltage of the device can increase.

Next, a hole blocking layer ("HBL") 180 can be formed on a surface of the EML 140 using a vacuum deposition method, a spin coating method, a casting method, LB, or the like. The hole blocking layer is used to prevent diffusion of triplet excitons formed in the material of the emitting layer 140 from migrating to the electron transport layer 150, or prevents holes from migrating into an electron transport layer 150 when the phosphorescent dopant is used to form the EML 140. When the HBL 180 is formed by vacuum deposition or spin coating, conditions for deposition and coating are similar to those used for the formation of the HIL 120, although conditions for deposition and coating conditions may vary according to the material used to form the HBL 180.

In one embodiment, suitable material used to form the HBL 180 include, for example, imidazole derivatives, oxadiazole derivatives, triazole derivatives, a phenanthroline derivative, e.g., 2,9-dimethyl-4,7-diphenyl phenanthroline, 2,9-dimethyl-4,7-diphenyl-1,10-phenanthroline "BCP"), an aluminum complex, such as bis(2-methyl-8-quinolinolato)-aluminum biphenolate ("BAlq"), or the like, as represented by the following organic compounds:

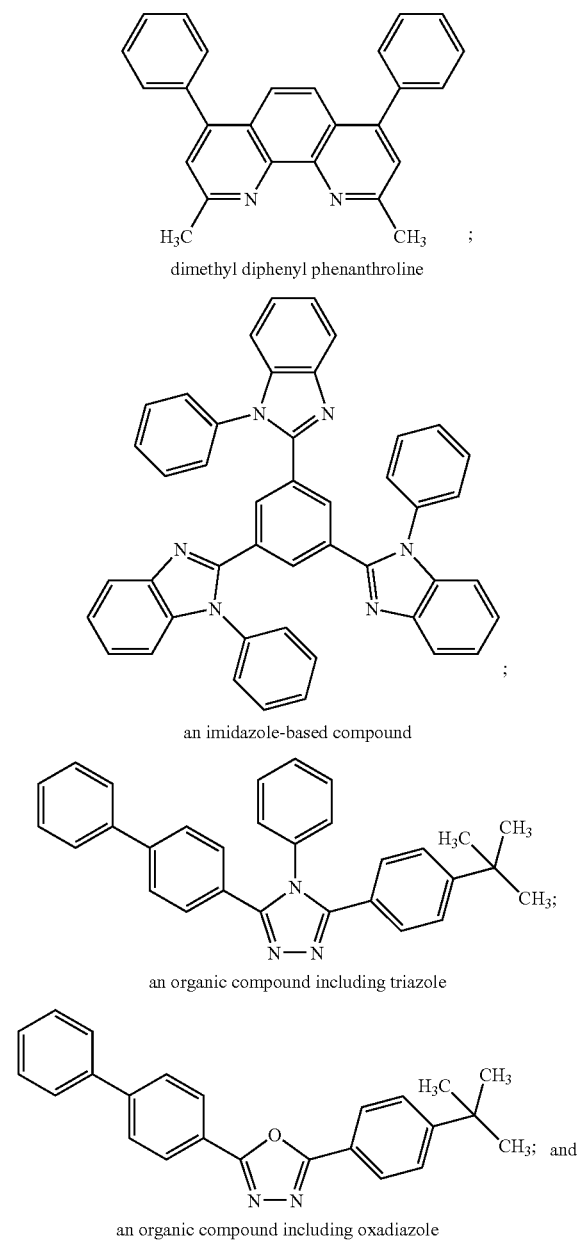

dimethyl diphenyl phenanthroline an imidazole-based compound an organic compound including triazole an organic compound including oxadiazole -continued

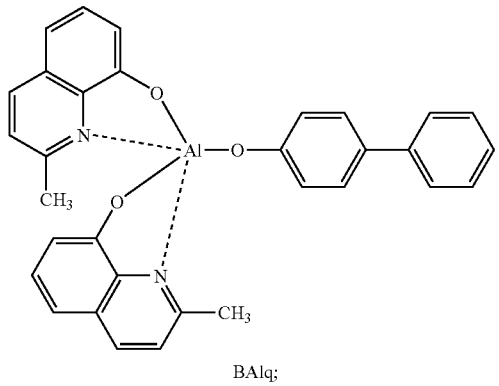

BAlq;

The thickness of the HBL 180 may be from about 50 to about 1,000 Å, and preferably, from about 100 to about 300 Å. When the thickness of the HBL 180 is less than about 50 Å, hole blocking capability may be reduced. On the other hand, when the thickness of the HBL 180 is greater than about 1,000 Å, the driving voltage of the device can increase.

Then, an electron transport layer ("ETL") 150 is formed on a surface of the HBL 180 opposite the EML 140 by vacuum deposition, spin coating, casting, or the like. When the ETL is formed by vacuum deposition and spin coating, conditions for deposition and coating are, in general, similar to those used for formation of the HIL 120, although conditions for deposition and coating conditions may vary according to the material used to form the ETL 150.

Examples of suitable material used to form the ETL 150 includes, for example, oxazole-based compounds, isooxazole-based compounds, triazole-based compounds, isothiazole-based compounds, oxadiazole-based compounds, thiadiazole-based compounds, perylene-based compounds, aluminum complexes, such as tris(8-quinolinolato)-aluminum ("Alq3"), BAlq, bis(2-methyl-8-quinolinolato)-aluminum triphenylsilicide ("SAlq") and tris(2-methyl-8-quinolinolato)-aluminum ("Almq3"), gallium complexes such as bis (2-methyl-8-quinolinolato)-gallium pivalate ("Gaq'2OPiv"), bis(2-methyl-8-quinolinolato)-gallium acetate ("Gaq'2OC"), and μ-oxo-bis[bis(2-methyl-8-quinolinolato)-gallium] ("2 (Gaq'2)"), or the like, which stably transports injected electrons from cathode, which is known in the art. Examples of suitable materials used to form the ETL 150 are represented by the following organic compounds:

a perylene-based compound:

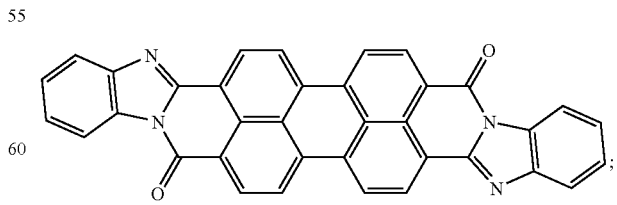

-continued

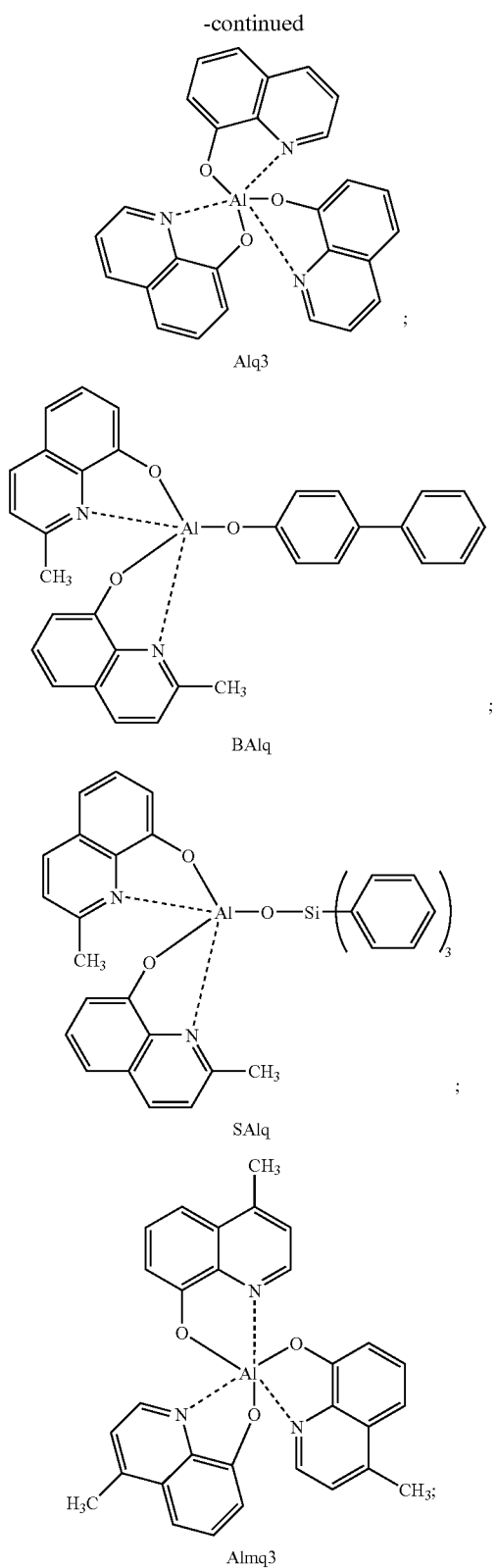

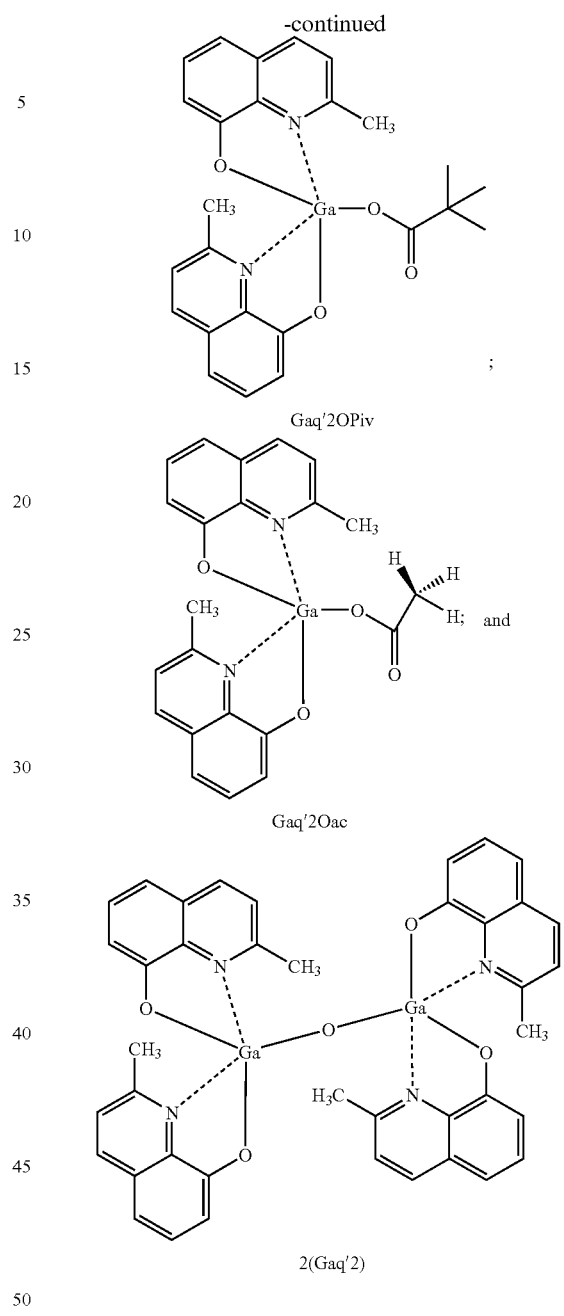

The thickness of the ETL 150 may be from about 100 to about 1,000 Å, and preferably, about 200 to about 500 Å. When the thickness of the ETL 150 is less than about 100 Å, electron transporting capability may be reduced. On the other hand, when the thickness of the ETL 150 is greater than about 1,000 Å, the driving voltage of the device can increase.

Then, an electron injection layer ("EIL") 160, which is formed of a material allowing easy injection of electrons from a cathode, can be formed on a surface of the ETL 150 opposite the HBL 180. The material that is used to form the EIL 160 is not limited.

Suitable materials used to form the EIL 160 include, for example, LiF, NaCl, CsF, $Li_2O$, BaO, or any other material conventionally used to form EIL 160 which is known in the art. Conditions for depositing the EIL 160 are, in general, similar to the conditions used for formation of the HIL 120, although they may vary according to the material used to form the EIL 160.

The thickness of the EIL 160 may be from about 1 to about 100 Å, and preferably, about 5 to about 50 Å. When the thickness of the EIL 160 is less than about 1 Å, electron injecting capability may be reduced. On the other hand, when the thickness of the EIL 160 is greater than about 100 Å, the driving voltage of the device can increase.

Finally, a second electrode 170 can be formed on a surface of the EIL 160 opposite the ETL 150 by vacuum deposition, sputtering, or the like. The second electrode can be used as a cathode. In one embodiment, the material that is used to form the second electrode 170 can be a metal, a low work-function metal, an alloy, an electrically conductive compound, or a combination thereof. Examples of suitable materials that can be used to form the second electrode 170 include Li, Mg, Al, Al—Li, Ca, Mg—In, Mg—Ag, or the like. In addition, a transparent cathode (not shown) formed of ITO or IZO and in contact with the second electrode 170 can be used to produce a front surface light emitting device.

The present invention will now be described in further detail with reference to the following examples. The following examples and are for illustrative purposes and thus are not intended to limit the scope of the invention.

EXAMPLES

Synthesis Example 1

Preparation of a Compound Represented by Formula 3

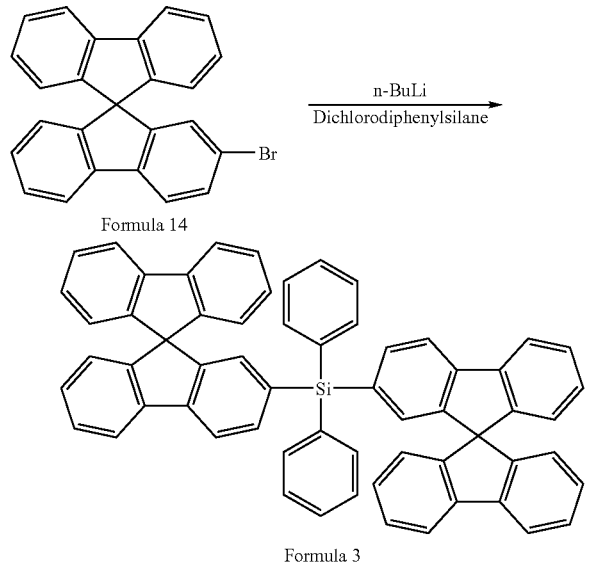

2-bromo-9,9'-spirobifluorene (Formula 14) which is an intermediate was synthesized using a method introduced in *The Journal of Organic Chemistry* 2002, vol. 67, pp. 4924-4936. Then, 2.0 g (5.06 mmol) of compound of Formula 14 was dissolved in 100 ml of tetrahydrofuran ("THF"), and 3.5 ml (5.6 mmol) of n-BuLi and 0.63 g (2.49 mmol) of dichlorodiphenylsilane were added thereto at −78° C. The temperature was gradually increased to room temperature and the mixture was allowed to react for 18 hours. The solvent was evaporated under reduced pressure and the resulting material was purified using silica gel column chromatography and as an eluant, a solution of chloroform and hexane (1:1 v/v) to produce 1.61 g of Formula 3 (Yield 70%).

Synthesis Example 2

Preparation of a Compound Represented by Formula 4

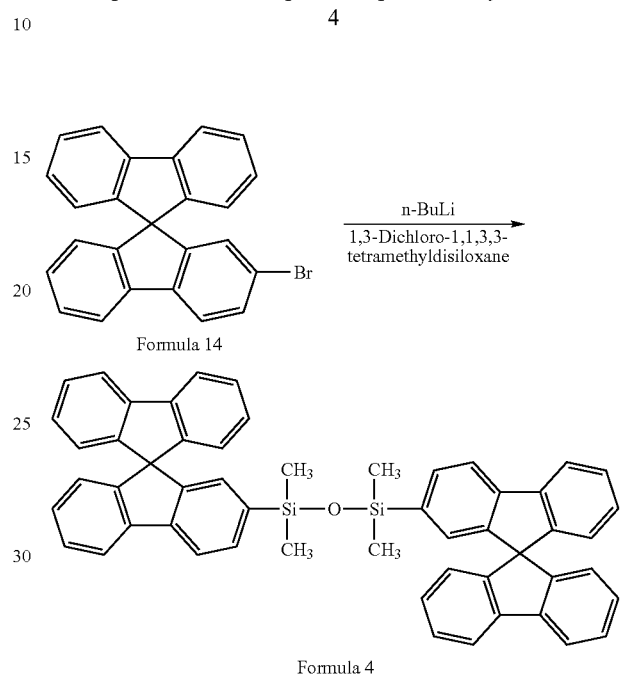

1.12 g of the compound represented by Formula 4 was produced in the same manner as in Synthesis Example 1, except that 1,3-dichloro-1,1,3,3-tetramethyldisiloxane was used instead of dichlorodiphenylsilane (Yield 59%).

Synthesis Example 3

Preparation of a Compound Represented by Formula 5

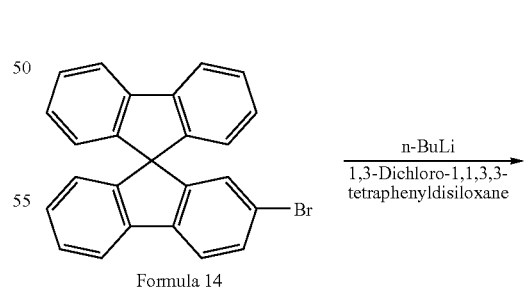

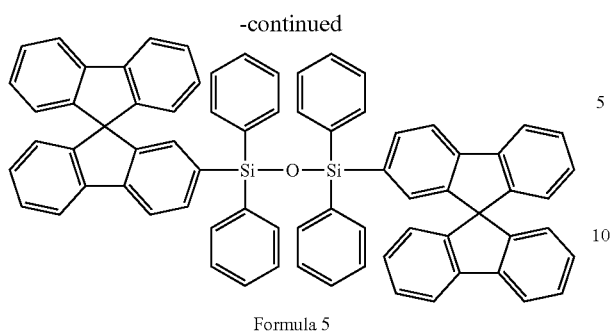

Formula 5

1.65 g of the compound represented by Formula 5 was produced in the same manner as in Synthesis Example 1, except that 1,3-dichloro-1,1,3,3-tetraphenyldisiloxane was used instead of dichlorodiphenylsilane (Yield 65%).

Synthesis Example 4

Preparation of a Compound Represented by Formula 6

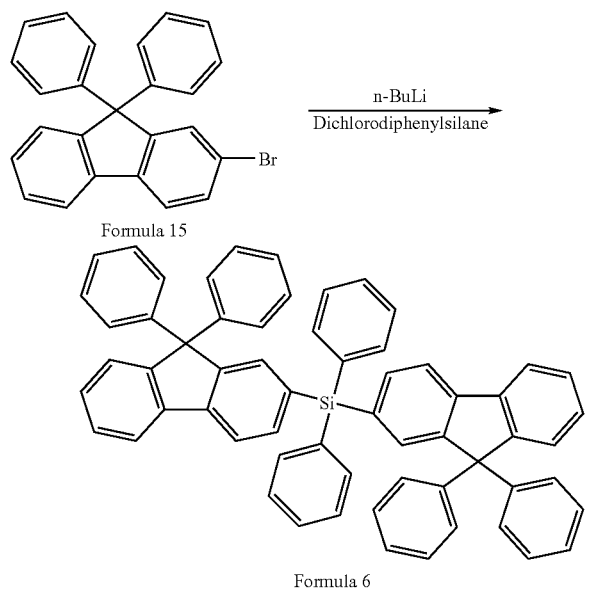

Formula 6

2-bromo-9,9'-diphenylfluorene (represented by Formula 15) which is an intermediate was synthesized using a method introduced in *Organic Letters* 2002, vol. 4, No. 25, pp. 4439-4442. Then, 2.01 g (5.06 mmol) of Formula 15 was dissolved in 100 ml of THF, and 3.5 ml (5.6 mmol) of n-BuLi and 0.63 g (2.49 mmol) of dichlorodiphenylsilane were added thereto at −78° C. The temperature was gradually increased to room temperature and the mixture was reacted for 18 hour. The solvent was evaporated under reduced pressure and the result was purified using silica gel column chromatography, and as an eluant, a solution of chloroform and hexane (1:1 v/v) to produce 1.69 g of a compound of Formula 6 (Yield 83%).

Synthesis Example 5

Preparation of a Compound Represented by Formula 7

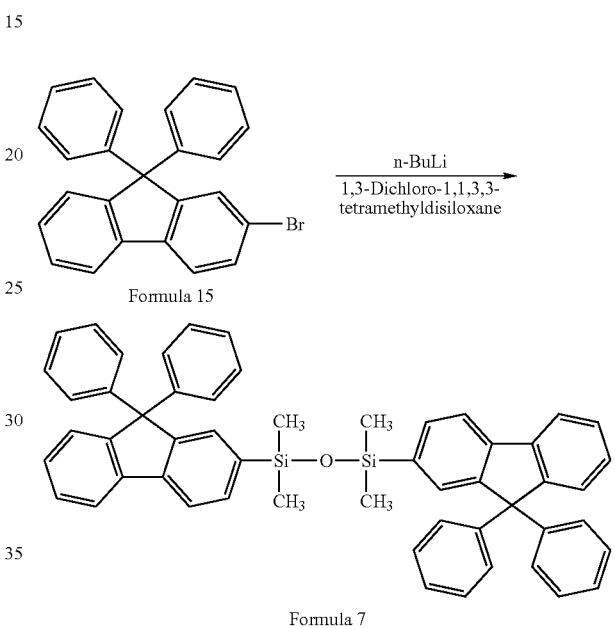

Formula 7

1.24 g of the compound represented by Formula 7_was produced in the same manner as in Synthesis Example 4, except that 1,3-dichloro-1,1,3,3-tetramethyldisiloxane was used instead of dichlorodiphenylsilane (Yield 65%).

Synthesis Example 6

Preparation of a Compound Represented by Formula 8

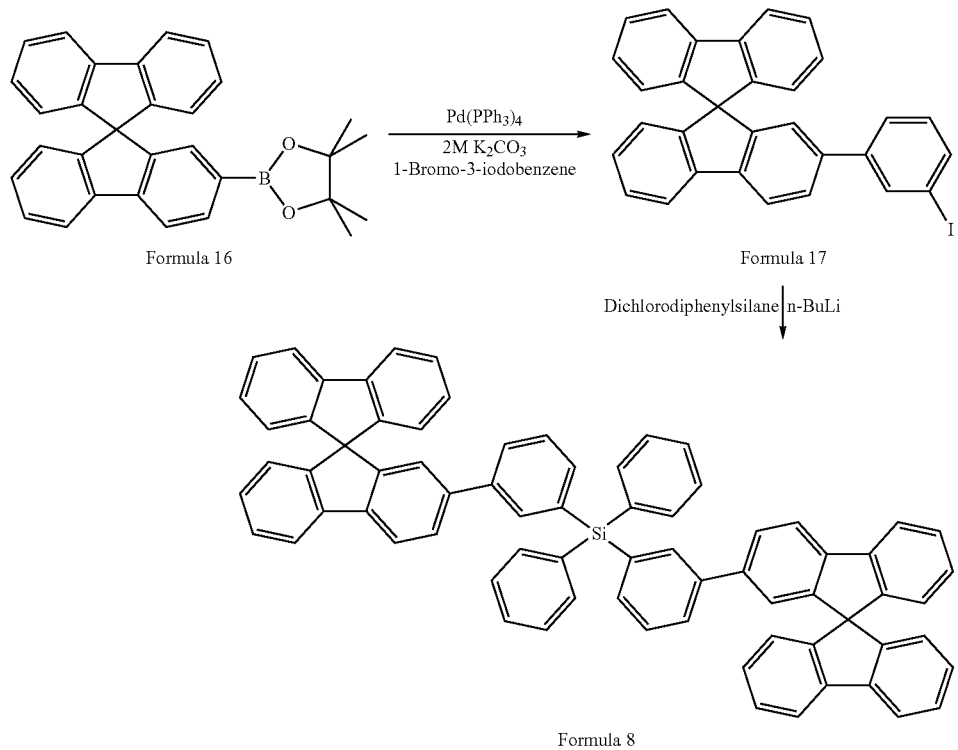

Formula 8

2-pinacolato boronic ester-9,9'-spirobifluorenes (represented by Formula 16) which is an intermediate was synthesized using a method introduced in *Organic Letters* 2005, vol. 7, No. 23, pp. 5131-5134. 3.0 g (6.78 mmol) of a compound represented by Formula 16 was dissolved in 100 ml of THF, and 0.77 g (0.67 mmol) of Pd(PPh$_3$)$_4$, 15 ml (30 mmol) of 2M K$_2$CO$_3$, and 1.918 g (6.78 mmol) of 1-bromo-3-iodobenzene were added thereto. The temperature was increased to 90° C. and the mixture was reacted while refluxing for 24 hours. The solvent was evaporated under reduced pressure and the result was purified using silica gel column chromatography, and as an eluant, a solution of chloroform and hexane (1:1 v/v) to produce 2.6 g of a compound of Formula 17 (Yield 74%). 2.62 g (5.06 mmol) of the obtained compound represented by Formula_17 was dissolved in 100 ml of THF, and 3.5 ml (5.6 mmol) of n-BuLi and 0.63 g (2.49 mmol) of dichlorodiphenylsilane were added thereto at −78° C. The temperature was gradually increased to room temperature and the mixture was reacted for 18 hour. The solvent was evaporated under reduced pressure and the result was purified using a silica gel column chromatography, and as an eluant, a solution of chloroform and hexane (1:1) to produce 1.56 g of compound represented by Formula 8 (Yield 65%).

Synthesis Example 7

Preparation of a Compound Represented by Formula 9

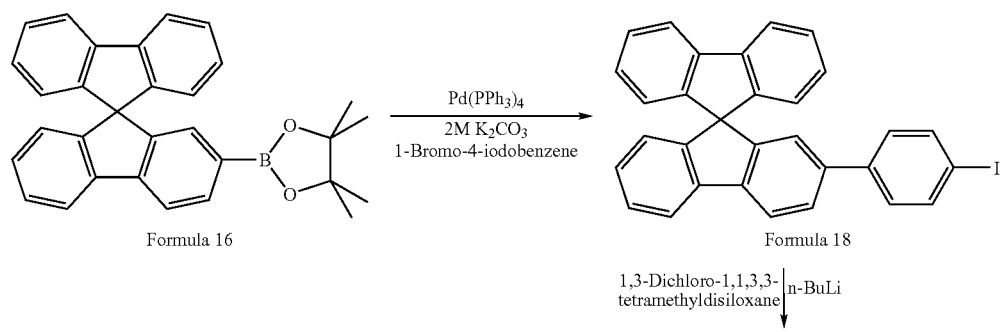

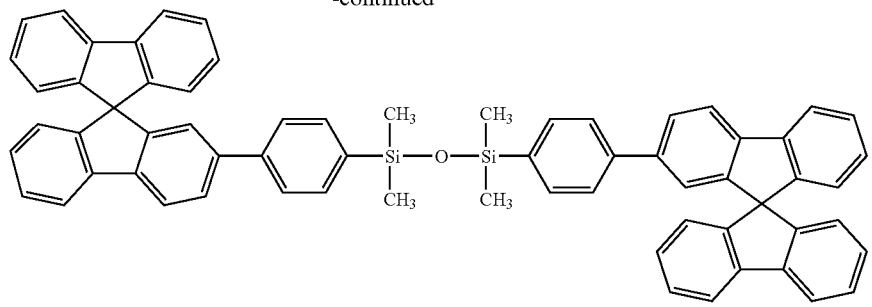

Formula 9

1.23 g of a compound represented by Formula 9 was produced in the same manner as in Synthesis Example 6, except that 1-bromo-4-iodobenzene was used instead of 1-bromo-3-iodobenzene to obtain a compound represented by Formula 18 and 1,3-dichloro-1,1,3,3-tetramethyldisiloxane was used instead of dichlorodiphenylsilane (Yield 54%).

Synthesis Example 8

Preparation of a Compound Represented by Formula 10 dibromonaphtalene was used instead of 1-bromo-3-iodobenzene and 1.61 g of a compound represented by Formula 10 was obtained using the obtained compound represented by Formula 19 using the same method of synthesizing compound represented by Formula 8 (Yield 60%).

Synthesis Example 9

Preparation of a Compound Represented by Formula 11

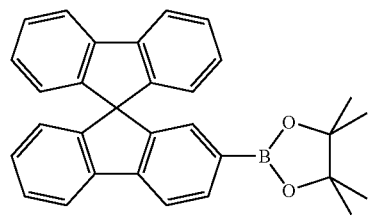

Formula 16

Pd(PPh₃)₄
2M K₂CO₃
2,6-Dibromonaphthalene

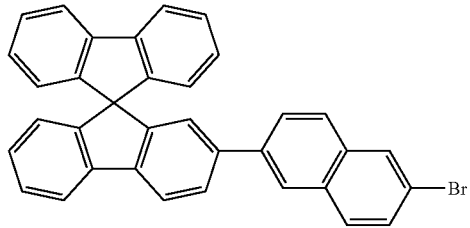

Formula 19

Dichlorodiphenylsilane | n-BuLi

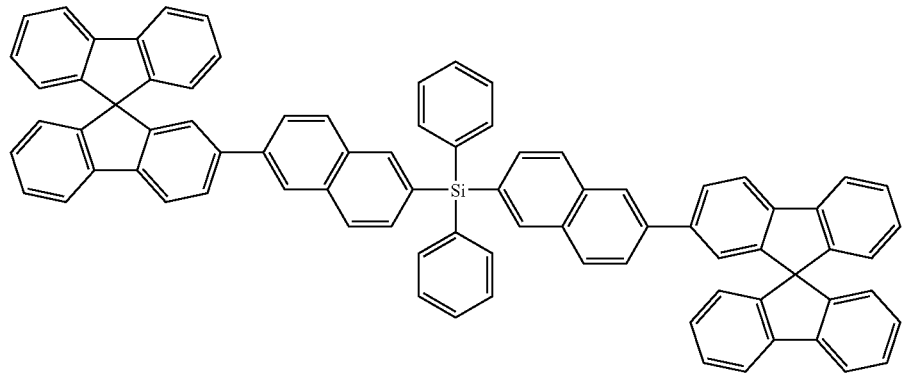

Formula 10

Compound represented by Formula 19 was produced in the same manner as in Synthesis Example 6, except that 2,6-

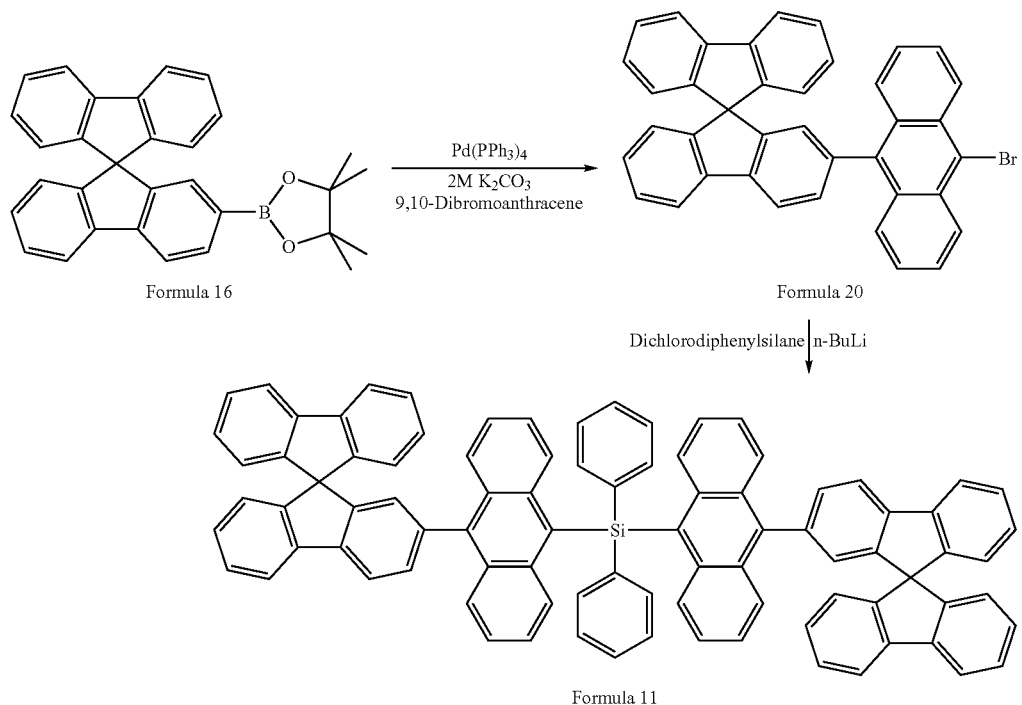

A compound represented by Formula 20 was produced in the same manner as in Synthesis Example 6, except that 9,10-dibromoanthracene was used instead of 1-bromo-3-iodobenzene and 1.36 g of a compound represented by Formula 11 was obtained using the obtained compound represented by Formula 20, and using the same method in Synthesis Example 6 for producing the compound represented by Formula 8 (Yield 47%).

Synthesis Example 10

Preparation of a compound represented by Formula 12

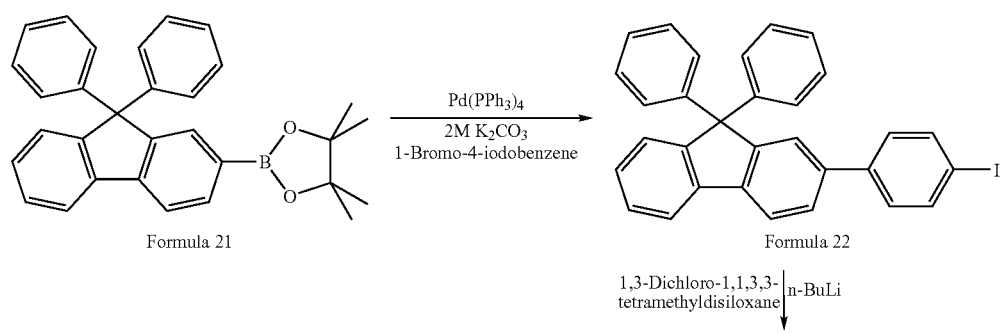

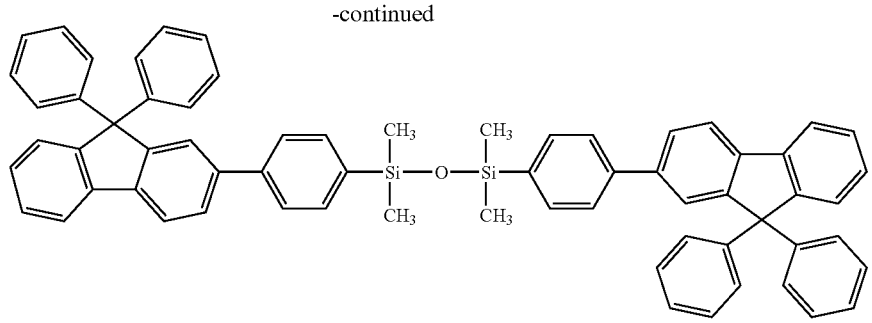

Formula 12

2-pinacolato boronic ester-9,9'-diphenylfluorene (compound represented by Formula 21) which is an intermediate was synthesized using a method introduced by *Organic Letters* 2002, vol. 4, No. 25, pp. 4439-4442. Compounds represented by Formulas 22 and 12 were produced in the same manner as Synthesis Example 7 using compound represented by Formula 21 (1.40 g, Yield 61%).

Synthesis Example 11

Preparation of a Compound Represented by Formula 13 was evaporated under reduced pressure, and the result was purified using a silica gel column chromatography to produce 2.67 g of a compound represented by Formula 23 (Yield 72%). 2.77 g (5.06 mmol) of the obtained compound represented by Formula 23 was dissolved in 100 ml of THF, and 3.5 ml (5.6 mmol) of n-BuLi and 0.63 g (2.49 mmol) of dichlorodiphenylsilane were added thereto at −78° C. The temperature was gradually increased to room temperature and the mixture was reacted for 18 hour. The solvent was evaporated under reduced pressure and the result was purified using a silica gel column chromatography, and as an eluant, a solution of chloroform and hexane (1:1 v/v) to produce 1.28 g of

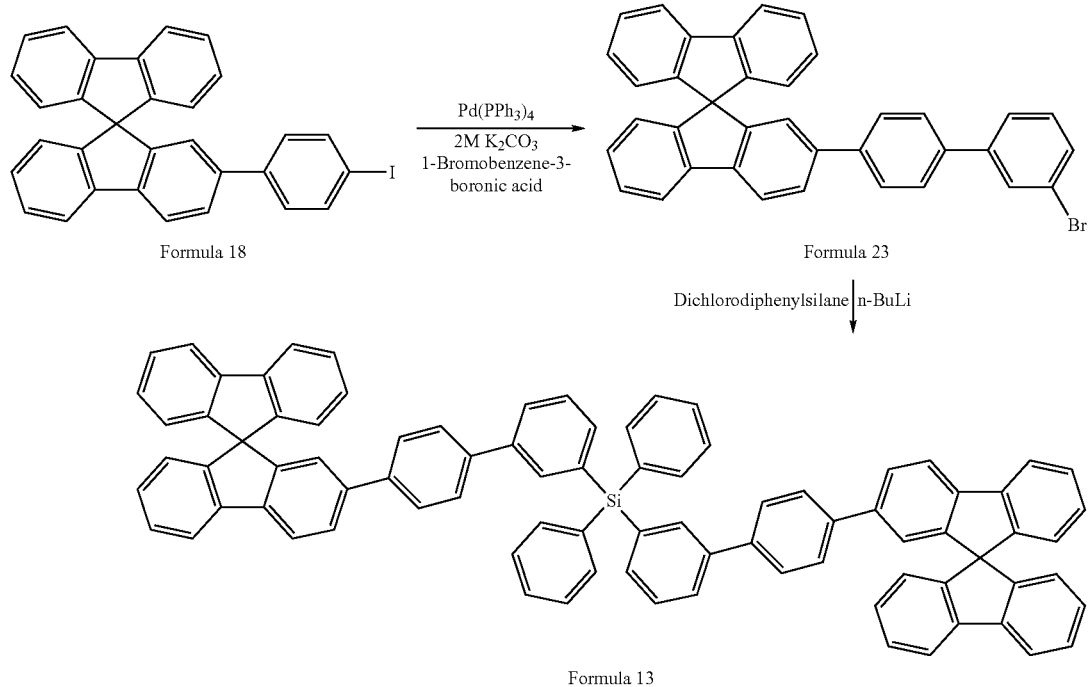

3.514 g (6.78 mmol) of compound represented by Formula 18 was dissolved in 100 ml of THF, and 0.77 g (0.67 mmol) of Pd(PPh$_3$)$_4$, 15 ml (30 mmol) of 2M K$_2$CO$_3$, and 1.918 g (6.78 mmol) of 1-bromobenzene-3-boronic acid were added thereto. The temperature was increased to 90° C., and the mixture was reacted while refluxing for 24 hours. The solvent Compound 21 (Yield 46%). The structures of all of the synthesized compounds represented by Formulas 3 through 13 were identified using $^1$H NMR and liquid chromatography-mass spectrometry (LC-MS).

Measurement Example

Optical Properties of Materials

Luminous properties of the obtained compounds were measured using photoluminescence ("PL") spectra in solution phase and film phase. To measure optical properties of the solution phase, the PL spectrum of a 10 mM of the compounds diluted in toluene was obtained using an ISC PC1 spectrofluorometer having a Xenon lamp. To measure optical properties of the film phase, a quartz substrate was washed with acetone and pure water. The individual compound was spin coated on the quartz substrate and heat treated at 110° C. for 30 minutes to form a film with 1,000 Å thickness. The PL spectrum of the film was measured. The results are shown in Table 1 and it was identified that the Material according to the present invention had light emitting properties suitable for organo-electroluminescent devices through the results.

TABLE 1

| Compound of Formula: | Solution ($\lambda_{max}$) (nm) | Film ($\lambda_{max}$) (nm) |
|---|---|---|
| 3 | 322, 334 | 327, 339 |
| 4 | 321, 333 | 326, 338 |
| 5 | 325, 340 | 335, 350 |
| 6 | 322, 334 | 326, 338 |
| 7 | 321, 333 | 326, 338 |
| 8 | 340, 358 | 350, 368 |
| 9 | 339, 357 | 342, 360 |
| 10 | 355, 372 | 360, 377 |
| 11 | 390, 410 | 400, 420 |
| 12 | 338, 356 | 341, 359 |
| 13 | 363, 381 | 368, 386 |

Example 1

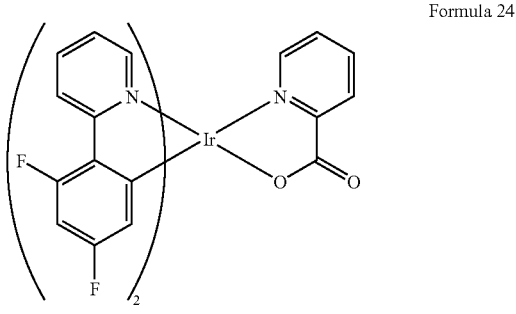

FIrpic

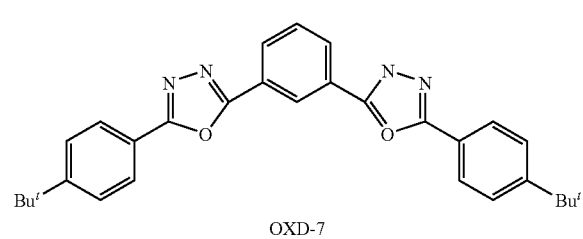

OXD-7

An organo-electroluminescent device having the following structure of a first electrode/HIL/EML/HTL/HIL/second electrode (as described in FIG. 1B) was manufactured using Materials described above as a host of an EML and the compound represented by Formula 24 as a dopant of an EML:ITO (1000 Å)/(PEDOT/PSS) (500 Å)/(45% by weight PVK—50% by weight of Material of the present invention—5% by weight of Firpic (800 Å)/OXD-7 (200 Å)/LiF (10 Å)/Al (150 Å).

A 15Ω/cm$^2$ (1000 Å) ITO glass substrate was cut to a size of 50 mm×50 mm×0.7 mm, microwave washed with acetone isopropyl alcohol for 15 minutes, microwave washed with pure water for 15 minutes, and washed with UV ozone for 30 minutes. PEDOT-PSS was spin coated on the surface of the substrate with a thickness of 500 Å. Next, PVK, a material of the present invention, and Firpic were mixed in the ratio of 45% by weight/50% by weight/5% by weight and the mixture was dissolved in toluene. The dissolved mixture was spin coated on the surface of the PEDOT-PSS layer to form an EML with a thickness of 800 Å. Then, an OXD-7 compound was vacuum deposited on the surface of the EML to form an ETL with a thickness of 200 Å. LiF was vacuum deposited on the surface of the ETL to form an EIL with a thickness of 10 Å, and then Al was vacuum deposited on the surface of the EIL to form a cathode with a thickness of 150 Å. As a result, an organo-electroluminescent device illustrated in FIG. 1B was manufactured. The properties of the organo-electroluminescent device are shown in Table 2.

TABLE 2

| | EL Property | | | |
|---|---|---|---|---|
| Formula | Maximum EL wavelength ($\lambda_{max}$) | External Quantum Efficiency (%) | Efficiency at the current density of 3 mA/cm$^2$ (cd/A) | Efficiency at the voltage of 10 V (cd/A) |
| 3 | 477 | 5.9 | 10.8 | 11.5 |
| 4 | 478 | 5.8 | 10.4 | 10.7 |
| 5 | 475 | 6.2 | 12.9 | 13.1 |
| 6 | 474 | 6.1 | 12.1 | 12.3 |
| 7 | 473 | 3.4 | 6.6 | 6.7 |
| 9 | 479 | 4.5 | 7.2 | 7.3 |
| 11 | 478 | 4.7 | 9.0 | 9.2 |
| 13 | 476 | 4.1 | 8.4 | 8.7 |

Example 2

An organo-electroluminescent device having the following structure of a first electrode/HIL/HTL/EML/HTL/HIL/second electrode (as described in FIG. 1A) was manufactured using materials described above as a host of an EML and Compound 14 as a dopant of an EML: ITO(1000 Å)/(PEDOT/PSS) (500 Å)/(TCTA (400 Å)/(93% by weight of Material of the present invention—7% by weight Firpic)(300 Å)/TPBI (200 Å)/LiF (10 Å)/Al (150 Å). Here, TCTA is 4,4',4''-tri(N-carbazolyl)triphenylamine which is used as a HTL, TPBI is 2,2',2''-(1,3,5-benzenetriyl)tris[1-phenyl-1H-benzimidazole] which is used as an ETL.

A 15 Ω/cm$^2$ (1000 Å) ITO glass substrate was cut to a size of 50 mm×50 mm×0.7 mm, microwave washed with acetone isopropyl alcohol for 15 minutes, microwave washed with pure water for 15 minutes, and washed with UV ozone for 30 minutes. PEDOT-PSS was spin coated on the surface of the substrate to a thickness of 500 Å, and TCTA was vacuum deposited thereon to a thickness of 400 Å. Material of the present invention/Firpic (in a proportion of 93% by weight/7% by weight) was vacuum deposited thereon to form an EML with a thickness of 300 Å. Then, a TPBI compound was vacuum deposited on the surface of the EML to form an ETL with a thickness of 300 Å. LiF was vacuum deposited on the surface of the ETL to form an EIL with a thickness of 10 Å, and then Al was vacuum deposited on the EIL to form a cathode with a thickness of 150 Å. As a result, an organo-electroluminescent device illustrated in FIG. 1A was manufactured. The properties of the organo-electroluminescent device are shown in Table 3.

TABLE 3

| Formula | EL Property | | | |
|---|---|---|---|---|
| | Maximum EL wavelength ($\lambda_{max}$) | External Quantum Efficiency (%) | Efficiency at the current density of 3 mA/cm$^2$ (cd/A) | Efficiency at the voltage of 10 V (cd/A) |
| 3 | 474 | 9.8 | 18.4 | 18.5 |
| 5 | 474 | 10.5 | 19.1 | 19.3 |
| 8 | 477 | 7.8 | 13.1 | 13.5 |
| 13 | 477 | 7.6 | 12.8 | 13.1 |

As shown in Examples, the compounds according to the present invention had excellent electroluminance properties and are suitable for phosphorescent and fluorescent materials.

A compound represented by Formula 1 or 2 has excellent thermal stability and light emitting capability and can be manufactured through dry and wet processes. Therefore, an organo-electroluminescent device having excellent properties in color purity, driving voltage, and internal and external light emitting efficiency can be obtained by employing the fluorene-based compound of the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A fluorene-based compound represented by Formula 1 below:

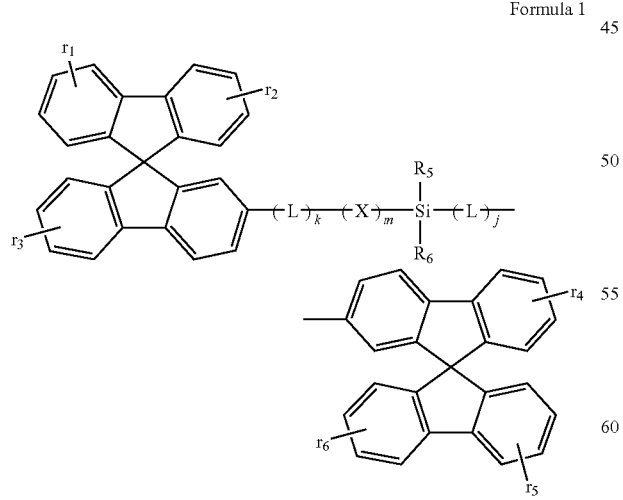

Formula 1 where L is selected from the group consisting of a substituted or unsubstituted $C_2$~$C_{30}$ alkylene group, a substituted or unsubstituted $C_6$~$C_{30}$ cycloalkylene group, a substituted or unsubstituted $C_6$~$C_{30}$ arylene group, a substituted or unsubstituted $C_2$~$C_{30}$ heteroarylene group, and a substituted or unsubstituted $C_2$~$C_{30}$ alkenylene group;

k is an integer from 0 to 2, j is an integer from 0 to 2,

X is

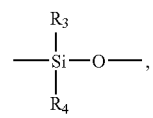

where $R_3$ and $R_4$ are each independently selected from the group consisting of a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, and a substituted or unsubstituted $C_2$~$C_{30}$ heteroaryl group;

m is an integer from 1 to 3, $R_5$ and $R_6$ are each independently selected from the group consisting of a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$ $C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, and a substituted or unsubstituted $C_2$~$C_{30}$ heteroaryl group;

$r_1$, $r_2$, $r_3$, $r_4$, $r_5$ and $r_6$ are each independently selected from the group consisting of a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, and a substituted or unsubstituted $C_2$~$C_{30}$ heteroaryl group.

2. A fluorene-based compound represented by Formula 2 below:

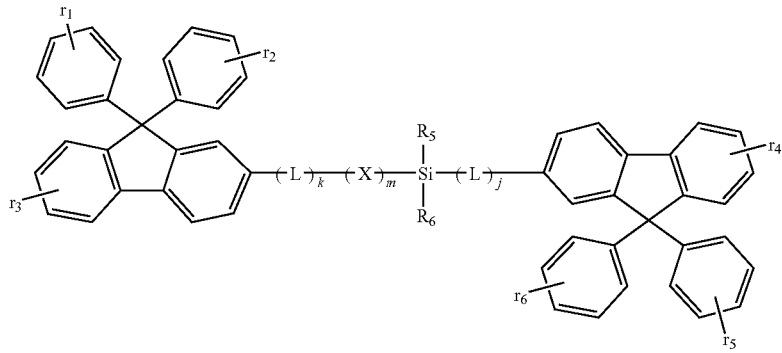

Formula 2 where L is selected from the group consisting of a substituted or unsubstituted $C_2$~$C_{30}$ alkylene group, a substituted or unsubstituted $C_6$~$C_{30}$ cycloalkylene group, a substituted or unsubstituted $C_6$~$C_{30}$ arylene group, a substituted or unsubstituted $C_2$~$C_{30}$ heteroarylene group, and a substituted or unsubstituted $C_2$~$C_{30}$ alkenylene group;

k is an integer from 0 to 2,
j is an integer from 0 to 2,
X is

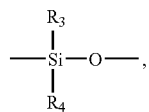

where $R_3$ and $R_4$ are each independently selected from the group consisting of a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, and a substituted or unsubstituted $C_2$~$C_{30}$ heteroaryl group;

m is an integer from 1 to 3, $R_5$ and $R_6$ are each independently selected from the group consisting of a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, and a substituted or unsubstituted $C_2$~$C_{30}$ heteroaryl group;

$r_1$, $r_2$, $r_3$, $r_4$, $r_5$ and $r_6$ are each independently selected from the group consisting of a hydrogen atom, a halogen atom, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{30}$ heterocycloalkyl group, a substituted or unsubstituted $C_1$~$C_{20}$ alkoxy group, a substituted or unsubstituted $C_6$~$C_{30}$ aryl group, a substituted or unsubstituted $C_6$~$C_{30}$ aralkyl group, and a substituted or unsubstituted $C_2$~$C_{30}$ heteroaryl group.

3. The fluorene-based compound of claim 1, wherein the alkyl group, the alkoxy group, the aryl group, the aralkyl group, the heteroaryl group, the cycloalkyl group, and the heterocycloalkyl group in the Formulae 1 and 2 can be substituted and the substituent is at least one selected from the group consisting of —F, —Cl, —Br, —CN, —NO$_2$, and —OH; a $C_1$~$C_{20}$ alkyl group unsubstituted or substituted by —F, —Cl, —Br, —CN, —NO$_2$ or —OH, a $C_1$~$C_{20}$ alkoxy group unsubstituted or substituted by —F, —Cl, —Br, —CN, —NO$_2$ or —OH, a $C_6$~$C_{30}$ aryl group unsubstituted or substituted by —F, —Cl, —Br, —CN, —NO$_2$ or —OH, a $C_2$~$C_{30}$ heteroaryl group unsubstituted or substituted by —F, —Cl, —Br, —CN, —NO$_2$ or —OH, a $C_5$~$C_{20}$ cycloalkyl group unsubstituted or substituted by —F, —Cl, —Br, —CN, —NO$_2$ or —OH, and a $C_5$~$C_{30}$ heterocycloalkyl group unsubstituted or substituted by —F, —Cl, —Br, —CN, —NO$_2$ or —OH.

4. The fluorene-based compound of claim 2, wherein the alkyl group, the alkoxy group, the aryl group, the aralkyl group, the heteroaryl group, the cycloalkyl group, and the heterocycloalkyl group in the Formulae 1 and 2 can be substituted and the substituent is at least one selected from the group consisting of —F, —Cl, —Br, —CN, —NO$_2$, and —OH; a $C_1$~$C_{20}$ alkyl group unsubstituted or substituted by —F, —Cl, —Br, —CN, —NO$_2$ or —OH, a $C_1$~$C_{20}$ alkoxy group unsubstituted or substituted by —F, —Cl, —Br, —CN, —NO$_2$ or —OH, a $C_6$~$C_{30}$ aryl group unsubstituted or substituted by —F, —Cl, —Br, —CN, —NO$_2$ or —OH, a $C_2$~$C_{30}$ heteroaryl group unsubstituted or substituted by —F, —Cl, —Br, —CN, —NO$_2$ or —OH, a $C_5$~$C_{20}$ cycloalkyl group unsubstituted or substituted by —F, —Cl, —Br, —CN, —NO$_2$ or —OH, and a $C_5$~$C_{30}$ heterocycloalkyl group unsubstituted or substituted by —F, —Cl, —Br, —CN, —NO$_2$ or —OH.

5. The fluorene-based compound of claim 1, wherein the compound of Formula 1 is selected from the group consisting of compounds represented by any one of the Formulas below:

Formula 4

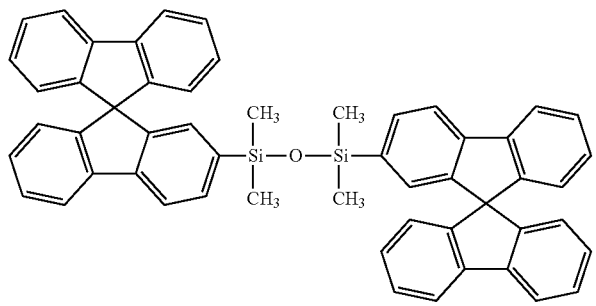

Formula 5

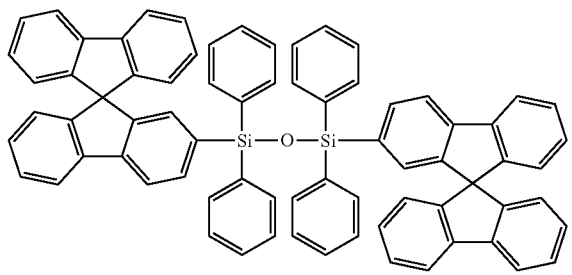

Formula 9

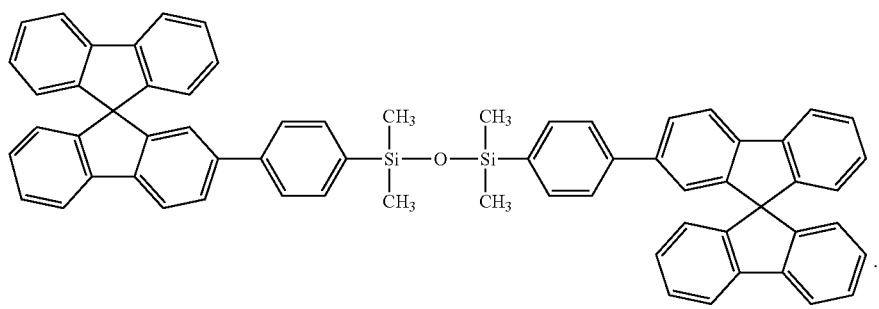

6. The fluorene-based compound of claim 2, wherein the compound of Formula 2 is selected from the group consisting of compounds of either of the Formulas below:

Formula 7

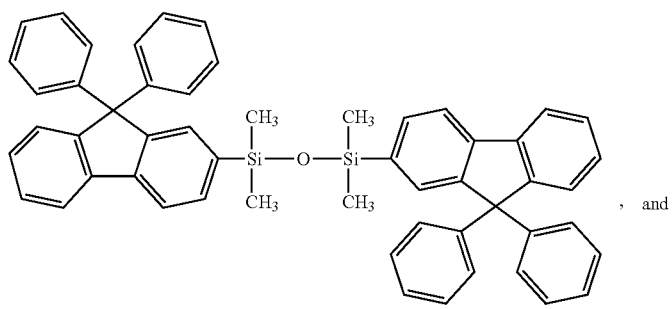

, and

Formula 12

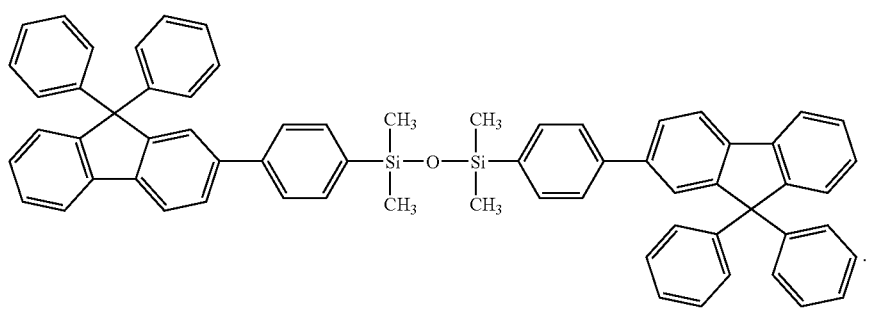

7. An organo-electroluminescent device comprising:
a first electrode;
a second electrode; and
at least one organic layer interposed between the first electrode and the second electrode,
wherein the organic layer comprises the fluorene-based compound of claim 1.

8. The organo-electroluminescent device of claim 7, wherein the organic layer is an emitting layer, a hole injection layer or a hole transport layer.

9. The organo-electroluminescent device of claim 7, further comprising at least one layer selected from the group consisting of a hole injection layer, a hole transport layer, an electron blocking layer, a hole blocking layer, an electron transport layer, and an electron injection layer.

10. The organo-electroluminescent device of claim 8, further comprising at least one layer selected from the group consisting of a hole injection layer, a hole transport layer, an electron blocking layer, a hole blocking layer, an electron transport layer, and an electron injection layer.

11. An organo-electroluminescent device comprising:
a first electrode;
a second electrode; and
at least one organic layer interposed between the first electrode and the second electrode,
wherein the organic layer comprises the fluorene-based compound of claim 2.

12. The organo-electroluminescent device of claim 11, wherein the organic layer is an emitting layer, a hole injection layer or a hole transport layer.

13. The organo-electroluminescent device of claim 11, further comprising at least one layer selected from the group consisting of a hole injection layer, a hole transport layer, an electron blocking layer, a hole blocking layer, an electron transport layer, and an electron injection layer.

14. The organo-electroluminescent device of claim 12, further comprising at least one layer selected from the group consisting of a hole injection layer, a hole transport layer, an electron blocking layer, a hole blocking layer, an electron transport layer, and an electron injection layer.

15. An organo-electroluminescent device comprising:
a first electrode;
a second electrode; and
at least one organic layer interposed between the first electrode and the second electrode,
wherein the organic layer comprises the fluorene-based compound of claim 3.

16. The organo-electroluminescent device of claim 15, wherein the organic layer is an emitting layer, a hole injection layer or a hole transport layer.

17. The organo-electroluminescent device of claim 15, further comprising at least one layer selected from the group consisting of a hole injection layer, a hole transport layer, an electron blocking layer, a hole blocking layer, an electron transport layer, and an electron injection layer.

18. The organo-electroluminescent device of claim 16, further comprising at least one layer selected from the group consisting of a hole injection layer, a hole transport layer, an electron blocking layer, a hole blocking layer, an electron transport layer, and an electron injection layer.

19. An organo-electroluminescent device comprising:
a first electrode;
a second electrode; and
at least one organic layer interposed between the first electrode and the second electrode,
wherein the organic layer comprises the fluorene-based compound of claim 4.

20. The organo-electroluminescent device of claim 19, wherein the organic layer is an emitting layer, a hole injection layer or a hole transport layer.

21. The organo-electroluminescent device of claim 19, further comprising at least one layer selected from the group consisting of a hole injection layer, a hole transport layer, an electron blocking layer, a hole blocking layer, an electron transport layer, and an electron injection layer.

22. The organo-electroluminescent device of claim 20, further comprising at least one layer selected from the group consisting of a hole injection layer, a hole transport layer, an electron blocking layer, a hole blocking layer, an electron transport layer, and an electron injection layer.

23. An organo-electroluminescent device comprising:
a first electrode;
a second electrode; and
at least one organic layer interposed between the first electrode and the second electrode,
wherein the organic layer comprises the fluorene-based compound of claim 5.

24. The organo-electroluminescent device of claim 23, wherein the organic layer is an emitting layer, a hole injection layer or a hole transport layer.

25. The organo-electroluminescent device of claim 23, further comprising at least one layer selected from the group consisting of a hole injection layer, a hole transport layer, an electron blocking layer, a hole blocking layer, an electron transport layer, and an electron injection layer.

26. The organo-electroluminescent device of claim 24, further comprising at least one layer selected from the group consisting of a hole injection layer, a hole transport layer, an electron blocking layer, a hole blocking layer, an electron transport layer, and an electron injection layer.

27. An organo-electroluminescent device comprising:
a first electrode;
a second electrode; and
at least one organic layer interposed between the first electrode and the second electrode,
wherein the organic layer comprises the fluorene-based compound of claim 6.

28. The organo-electroluminescent device of claim 27, wherein the organic layer is an emitting layer, a hole injection layer or a hole transport layer.

29. The organo-electroluminescent device of claim 27, further comprising at least one layer selected from the group consisting of a hole injection layer, a hole transport layer, an electron blocking layer, a hole blocking layer, an electron transport layer, and an electron injection layer.

30. The organo-electroluminescent device of claim 28, further comprising at least one layer selected from the group consisting of a hole injection layer, a hole transport layer, an electron blocking layer, a hole blocking layer, an electron transport layer, and an electron injection layer.

31. A method of making an organo-electroluminescent device comprising depositing:
an organic layer comprising the fluorene-based compound of claim 1 between a first electrode and a second electrode.

32. A method of making an organo-electroluminescent device comprising depositing:
an organic layer comprising the fluorene-based compound of claim 2 between a first electrode and a second electrode.

* * * * *